(12) United States Patent
Voix et al.

(10) Patent No.: US 11,771,372 B2
(45) Date of Patent: Oct. 3, 2023

(54) IN-EAR NONVERBAL AUDIO EVENTS CLASSIFICATION SYSTEM AND METHOD

(71) Applicant: ECOLE DE TECHNOLOGIE SUPERIEURE, Montreal (CA)

(72) Inventors: Jeremie Voix, Montreal (CA); Hami Montsarrat-Chanon, Montreal (CA); Rachel Bou Serhal, Montreal (CA); Patrick Cardinal, Kirkland (CA); Philippe Chabot, Lasalle (CA)

(73) Assignee: ECOLE DE TECHNOLOGIE SUPERIEURE, Montreal (CA)

( * ) Notice: Subject to any disclaimer, the term of this patent is extended or adjusted under 35 U.S.C. 154(b) by 0 days.

(21) Appl. No.: 16/759,502

(22) PCT Filed: Oct. 29, 2018

(86) PCT No.: PCT/CA2018/051369
§ 371 (c)(1),
(2) Date: Apr. 27, 2020

(87) PCT Pub. No.: WO2019/079909
PCT Pub. Date: May 2, 2019

(65) Prior Publication Data
US 2020/0312321 A1 Oct. 1, 2020

Related U.S. Application Data

(60) Provisional application No. 62/578,372, filed on Oct. 27, 2017.

(51) Int. Cl.
*A61B 5/00* (2006.01)
*G06N 20/00* (2019.01)
(Continued)

(52) U.S. Cl.
CPC .............. *A61B 5/6817* (2013.01); *G06F 3/16* (2013.01); *G06F 18/213* (2023.01);
(Continued)

(58) Field of Classification Search
CPC ... G10L 15/22; G10L 25/51; G10L 2015/227; G06N 20/00; G06F 3/16; G06K 9/6232; G06K 9/6268
See application file for complete search history.

(56) References Cited

U.S. PATENT DOCUMENTS 10,098,569 B2 * 10/2018 Abeyratne .............. G10L 25/66
11,147,502 B2 * 10/2021 Mohammadi ........ A61B 5/7203
(Continued)

FOREIGN PATENT DOCUMENTS

WO WO-2008149341 A2 * 12/2008 ........... A61B 5/4205
WO WO-2019119050 A1 * 6/2019 ........... A61B 5/0803

OTHER PUBLICATIONS

Anatomy and Development of the Mammalian External Auditory Canal: Implications for Understanding Canal Disease and Deformity (Year: 2021).*
(Continued)

*Primary Examiner* — Mohammad K Islam
(74) *Attorney, Agent, or Firm* — Brouillette Legal Inc.; Robert Brouillette

(57) ABSTRACT

A system and method for training a classification module of nonverbal audio events and a classification module for use in a variety of nonverbal audio event monitoring, detection and command systems. The method comprises capturing an in-ear audio signal from an occluded ear and defining at least one nonverbal audio event associated to the captured in-ear audio signal. Then sampling and extracting features from the in-ear audio signal. Once the extracted features are validated, associating the extracted features to the at least one
(Continued)

nonverbal audio event and updating the classification module with the association. The nonverbal audio event comprises one or a combination of user-induced or externally-induced nonverbal audio events such as teeth clicking, tongue clicking, blinking, eye closing, teeth grinding, throat clearing, saliva noise, swallowing, coughing, talking, yawning with inspiration, yawning with expiration, respiration, heartbeat and head or body movement, wind, earpiece insertion or removal, degrading parts, etc.

20 Claims, 19 Drawing Sheets

(51) Int. Cl.
  *G06F 3/16* (2006.01)
  *G10L 15/22* (2006.01)
  *G10L 25/51* (2013.01)
  *G06F 18/213* (2023.01)
  *G06F 18/21* (2023.01)
  *G06F 18/241* (2023.01)

(52) U.S. Cl.
  CPC .......... *G06F 18/217* (2023.01); *G06F 18/241* (2023.01); *G06N 20/00* (2019.01); *G10L 15/22* (2013.01); *G10L 25/51* (2013.01); *G10L 2015/227* (2013.01)

(56) References Cited

U.S. PATENT DOCUMENTS

| | | | |
|---|---|---|---|
| 2002/0171551 A1* | 11/2002 | Eshelman .......... | G08B 21/0453 340/573.1 |
| 2008/0253583 A1* | 10/2008 | Goldstein ................. | G06F 3/16 381/92 |
| 2011/0125063 A1* | 5/2011 | Shalon ................. | A61B 5/4205 600/590 |
| 2011/0276312 A1 | 11/2011 | Shalon et al. | |
| 2014/0235967 A1* | 8/2014 | LeBoeuf ................. | A61B 7/04 600/301 |
| 2015/0126825 A1* | 5/2015 | LeBoeuf ................. | A61B 5/029 600/301 |
| 2016/0073953 A1* | 3/2016 | Sazonov .............. | A61B 5/1107 600/590 |
| 2017/0147077 A1* | 5/2017 | Park ........................ | G06F 3/017 |
| 2017/0263266 A1* | 9/2017 | Henrique Barbosa Postal ............ | H04R 29/00 |
| 2019/0146747 A1* | 5/2019 | Usher .................... | H04R 1/406 704/233 |
| 2020/0253577 A1* | 8/2020 | Kj R Thing Riknagel ................ | A61B 7/00 |
| 2020/0267487 A1* | 8/2020 | Siva .......................... | H04S 7/30 |

OTHER PUBLICATIONS

A model of the occlusion effect with boneconducted stimulation (Year: 2007).*
Bone-Conducted Sound: Physiological and Clinical Aspects (Year: 2005).*
EESR dated Jun. 30, 2021 in the corresponding European Patent Application No. 18870393.8.

* cited by examiner

| Nonverbal Event | feature 1 | feature 2 | feature 3 | feature 4 | feature 5 | feature 6 |
|---|---|---|---|---|---|---|
| Blinking (slow) | 100 | 3 | 3000 | 375 | 27 | 10 |
| Blinking (regular) | 110 | 8 | 3010 | 376,25 | 72 | 20 |
| Blinking (fast) | 120 | 10 | 3100 | 387,5 | 90 | 30 |
| Chewing (soft) | 100 | 40 | 600 | 75 | 360 | 10 |
| Chewing (regular) | 110 | 45 | 607 | 75,875 | 405 | 20 |
| Chewing (fast) | 120 | 50 | 610 | 76,25 | 450 | 30 |
| Teeth Grinding (soft) | 100 | 60 | 1266 | 158,25 | 540 | 10 |
| Teeth Grinding (regular) | 110 | 65 | 1298 | 162,25 | 585 | 20 |
| Teeth Grinding (fast) | 120 | 70 | 1306 | 163,25 | 630 | 30 |
| Blinking and Sneezing | 200 | 86 | 2000 | 375 | 27 | 10 |
| Yawning and Breathing | 110 | 45 | 607 | 75,875 | 405 | 20 |
| Swallowing and Blinking | 100 | 60 | 1266 | 158,25 | 540 | 10 |

FIG 2

IN-EAR NONVERBAL AUDIO EVENTS CLASSIFICATION SYSTEM AND METHOD

CROSS-REFERENCE TO RELATED APPLICATIONS

The present patent application claims the benefits of priority of U.S. Provisional Patent Application No. 62/578,372, entitled "In-ear nonverbal audio events classification system and method" and filed at the United States Patent and Trademark Office on Oct. 27, 2017, the content of which is incorporated herein by reference.

TECHNICAL FIELD

The present generally relates to methods and systems to classify nonverbal audio events produced by humans and more particularly to methods and systems to classify nonverbal audio events that are captured from inside an occluded human ear canal.

BACKGROUND

The human body produces countless nonverbal audio events either in an uncontrolled manner such as heartbeats, respiration, etc., in a semi-controlled manner such as blinking of the eyes, coughing, throat clearing, etc. Detecting and identifying such nonverbal audio events can enable or enhance various applications such as health monitoring, artifact removal, silent speech interface, etc.

Health monitoring applications range from basic biosignal monitoring (ex.: monitoring of heart beat rate or breathing rate) to health, emotional or mental state assessment such as by monitoring disease-triggered events, or emotion-triggered events. Some known health monitoring applications rely on detecting and identifying nonverbal audio events that are produced by a physiological activity of the nervous system, be it from the sympathic or the parasympathic nervous system. For instance, as presented in co-pending International Patent Application No. PCT/CA2018/050453 by Martin et al., an audio signal is captured with a microphone that is placed inside the human ear-canal. The audio signal is filtered in the time domain using envelope filtering techniques to detect and identify audio events produced by the vascular system or the respiratory system. The identified audio event is analyzed in order to determine a heartbeat measurement, a respiration rate measurement or any other kind of attribute related to the vascular or respiratory system be it an attribute that is indicative of a health state (ex.: arrhythmia), an emotional state (ex.: cardiac coherence), a mental state, etc. The attribute of the identified audio event is determined according to information stored in a lookup dictionary. An inner audio signal is captured inside an ear canal of a user with an in-ear microphone. The audio signal is processed and one attribute of the inner audio signal is identified according to a predetermined audio signal association of the lookup dictionary. The attribute is limited to an association related to a heart rate and/or a breathing rate. Martin et al. rely on filtering audio signals to detect and identify audio events produced by the vascular system or the respiratory system. The application of a filter to identify a nonverbal audio event can be time consuming, require an extensive amount of processing power and can be inefficient, especially in applications where a variety of nonverbal audio event types must be specifically and accurately detected in real time.

Artifact removal applications aim at removing or disregarding irrelevant nonverbal audio events. Such irrelevant nonverbal audio events can in some cases affect the analysis of a captured audio signal, especially when the audio signal is captured from inside the ear canal. For instances, in US Patent Publication No. 2017/0150908 to Nadon et al. there is described an in-ear hearing health monitoring method and device. The method allows to determine the amount of environmental noise to which a wearer is exposed to when wearing a hearing protection device such as an earplug, by continuously monitoring the noise exposure of the wearer based on audio signals captured inside the ear-canal, for a given period of time. When in presence of wearer-generated disturbances, such as coughing, sneezing, chewing or gum chewing, teeth grinding, etc., the detected noise by the monitoring device can be erroneous since such wearer-generated disturbances can produce irrelevant large sound pressure levels that should not be considered in the noise exposure measurement, since wearer-generated disturbances are considered to be harmless to the hearing thanks to several biological and physiological protection mechanisms taking place in the middle and inner ear. In many cases, such wearer-generated disturbances must be identified and disregarded using an artifact removal method. The device described by Nadon et al. requires an internal microphone placed inside the ear canal, an external microphone that is placed within a distance of approximately 10 cm from the ear and an adaptive filter configured to disregard physiological noises produced by the wearer in order to provide a noise exposure measurement that is not influenced by the physiological noises of the wearer. The device requires filtering the captured in-ear audio signal according to audio signals captured from an external microphone and necessarily requires two microphones (i.e. the internal microphone and the external microphone). Moreover, the application of a filter to identify a physiological noise can be time consuming, require an extensive amount of processing power and can be inefficient, especially in applications where a variety of irrelevant physiological noise types must be specifically and accurately disregarded in real time.

Silent speech and nonverbal interfaces are a class of human-computer interfacing methods that do not rely respectively on audible speech or on speech. For instance, U.S. Pat. No. 6,503,197 to Nemirovski describes a method of detecting an action produced by the head of a user in order to generate a corresponding control signal. In U.S. Pat. No. 6,024,700 to Nemirovski et al. there is described a method of detecting a thought of a user in order to generate a response output. Nemirovski resorts to detecting an air pressure pattern near an ear of the user when the user is moving his head or when the user is thinking. The detection is passive. For instance, when trying to detect a head movement, a measured change in air pressure near the ear is used for detecting a tongue action produced by the user. Upon detection of a tongue action a corresponding output signal is generated by the system and the output signal may be used to control an external device such as a computer. Such system and method are limited at detecting changes in the air pressure near an ear and associating a measured air pressure to a head movement, a mouth movement, or a thought. The system and method are not capable of detecting and specifically identifying a variety nonverbal audio events from captured in-ear sound signals produced by a human user.

For instance, an in-ear device may be adapted to capture audio signals of nonverbal audio events, such as eye blinking, teeth clicking, etc. The nonverbal audio events can be produced by a wearer in a controlled manner in order to send commands inconspicuously to another device. The nonverbal audio events can also be produced by a wearer in an uncontrolled manner in order to send a life signal to another monitoring device.

Most systems and methods rely on filters to detect and identify a specific type of nonverbal audio event and cannot identify an extensive number of nonverbal audio events due to the limited processing power and real time communication constraints that must be considered in many cases. Some have resorted to the use of classifying captured sound signals in order to rapidly detect a predetermined limited group of events without using an extensive amount of processing power, however, those sound signals are captured in the environment and are different and much louder than sound signals that can be captured within an ear canal.

For instance, acoustic events such as gunshots, sirens and screams as well as people walking and closing doors have been classified for security purposes. However, those acoustic events are not related to inaudible or faint sounds. Humans can produce inaudible nonverbal audio events such as blinking or nonverbal faint sound events such as throat clearing, chewing, teeth clicking or grinding that would be advantageous to detect and identify for a variety of applications.

Therefore, there is a need for a method and system to accurately classify and detect an extensive variety of nonverbal audio events produced by a human without being limited to specific event types and that can be used with ease by a variety of applications.

SUMMARY

The shortcomings of the prior art are generally mitigated by a system and method for training and using a classification module of nonverbal audio events.

According to one aspect, there is a method for training a classification module of nonverbal audio events. The method comprises capturing an in-ear audio signal from an occluded ear. Defining at least one nonverbal audio event associated to the captured in-ear audio signal. Sampling the in-ear audio signal and extracting audio features from the sampled in-ear audio signal, then validating the extracted audio features. Once validated, associating the validated and extracted audio features to the at least one nonverbal audio event and updating the classification module with the association.

According to another aspect, there is a system for training a classification module of nonverbal audio events. The system comprises an electronic earpiece, an audio signal data storage module, a sampling module, a feature extraction module, a nonverbal audio event definer and a classification module. The earpiece has an in-ear microphone for capturing an audio signal from the ear canal. The audio signal data storage module is adapted to store the captured audio signal. The sampling module is adapted to sample the stored audio signal of the data storage module. The audio feature extraction module is adapted to extract a plurality of audio features from the sampled audio signal and validate the plurality of audio features. The nonverbal audio event definer is adapted to receive a nonverbal audio event definition corresponding to the captured audio signal. The classification module is adapted to be updated with the validated plurality of audio features in association with the received nonverbal audio event definition.

According to yet another aspect there is a method of determining a nonverbal audio event. The method comprises capturing an audio signal from an ear-canal, denoising the captured audio signal, classifying the denoised audio signal and identifying an associated nonverbal audio event according to the classified denoised audio signal.

The nonverbal audio event could be one or a combination of the following nonverbal audio events: teeth clicking, tongue clicking, blinking, eye closing, teeth grinding, throat clearing, saliva noise, swallowing, coughing, talking, yawning with inspiration, yawning with expiration, respiration, heartbeat and head or body movement, wind noise, earpiece manipulation such as insertion or removal from ear, degrading parts, etc.

Other and further aspects and advantages of the present invention will be obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The above and other aspects, features and advantages of the invention will become more readily apparent from the following description, reference being made to the accompanying drawings in which:

FIG. 2 is a table presenting the audio features of exemplary nonverbal audio events that are classified by the system of FIG. 1;

DETAILED DESCRIPTION OF THE PREFERRED EMBODIMENT

An in-ear nonverbal audio event classification system and method are described hereinafter. Although the system and method are described in terms of specific illustrative embodiments, it shall be understood that the embodiments described herein are by way of example only and that the scope of the present is not intended to be limited thereby. For instance, the following describes embodiments using an intra-aural hearing protection device, however it shall be recognized that the intra-aural hearing protection device can be replaced by any suitable electronic wearable in-ear device in general. For clarity, in the following description, the expressions "in-ear" and "intra-aural" are used interchangeably and are meant to refer to the auditory meatus region of the auditory canal of a human.

When the ear canal is blocked at the entry, energy builds-up from soft tissue and bone conduction. Such build-up causes amplification in sounds conducted by bones in the ear canal. The phenomenon is generally known as the occlusion effect. By way of an appropriate acoustic seal, intra-aural devices generally create an occlusion effect in the ear canal. Such acoustical seal provides a mean to access an extensive variety of human produced verbal and nonverbal audio events. In fact, the occluded ear is a reliable place to capture breathing and heart beat signals. Other relevant signals such as but not limited to blinking, coughing and clicking or grinding of the teeth can also be captured from inside the occluded ear.

Building of Classification System

Figure 1:
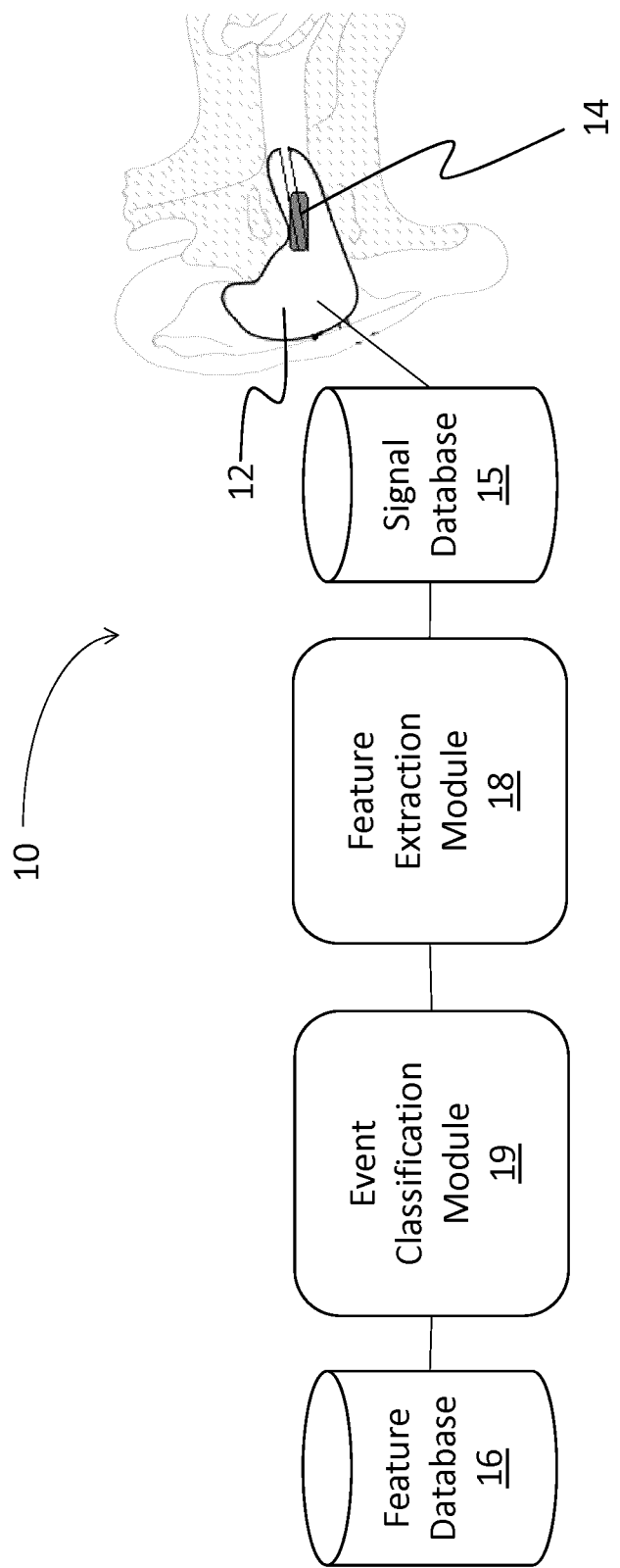
FIG. 1 is a diagram of a system for producing or training a classification module of nonverbal audio events by capturing in-ear audio signals, in accordance with one embodiment.

Presented in FIG. 1 is an in-ear nonverbal audio event classification system 10, according to one embodiment. The system 10 typically comprises an intra-aural hearing protection earpiece 12 such as an earplug. The earpiece 12 typically comprises an in-ear microphone 14 to capture audio signals of nonverbal audio events occurring in the occluded ear canal. The captured audio signals may be recorded using a recording device, such as a multi-channel digital audio recorder or any other suitable type of recorder. For instance, the recorder may use a sampling rate of 48 kHz and a sound resolution of 24-bit. It shall however be recognized that the sampling frequency, microphone and bit resolution can differ depending on the required audio signal accuracy and type of audio signal to be recorded.

The classification system 10 typically comprises a signal database 15 or data storage unit to store data used to store or describe the captured audio signals for one or more given nonverbal audio events. In one example, each captured audio signal is associated to at least one predetermined nonverbal audio event. Understandably, any type of signal database 15 or data storage unit may be used, such as transient or non-transient data source and/or embedded or remote data sources.

According to one embodiment, the classification system 10 comprises an audio feature extraction module 18 adapted to sample and extract audio features from at least one captured audio signal of the signal database 15, according to the at least one associated predetermined nonverbal audio event.

The classification system 10 may further comprise an audio feature association module 19 adapted to associate the extracted audio features to the predetermine nonverbal audio event and store the association in an audio feature database or audio data storage 16. In one example, the audio feature association module 19 is adapted to associate the extracted audio features to the predetermined nonverbal audio event, according to associations that have been previously stored in the audio feature database 16. In another example, the audio feature association module 19 is adapted to associate the extracted audio features to the predetermined nonverbal audio event according to another group of extracted audio features corresponding to the captured audio signal as stored in the signal database 15. In yet another example, the audio feature association module 19 is configured to associate the extracted audio features to the predetermined nonverbal audio event according to a validation result produced by another device.

For instance, while the wearer of the earpiece 12 is producing the predetermined or known nonverbal audio event, such as blinking, chewing, teeth clicking or grinding, etc., an audio signal from the ear canal is captured with the in-ear microphone 14. The captured audio signal is stored in the audio signal database 15. The audio feature extractor 18 samples and extracts the values of a predetermined group of audio features that are known to characterize the predetermined nonverbal audio event. The extracted audio feature values are validated by extracting another group of audio features from another sample of the captured signal and comparing the extracted audio feature values with the values of the other group of audio features. Understandably, the extracted audio features values may be validated by extracting audio features of another captured signal of the same known nonverbal audio event. Once validated, the event classification module 19 associates the audio feature values to the predetermined nonverbal audio event. The values are then stored in the audio feature database 16 as reference audio feature values and associated to the predetermined nonverbal audio event 20, as shown in FIG. 2. Notice that audio feature values related to a combination of nonverbal audio events 22 can also be store in the database.

In some embodiments, the captured nonverbal audio signals for classification may be associated to any of the following events: clicking of teeth softly (cts), clicking of teeth loudly (ctl), tongue clicking (cl), blinking forcefully (bf), closing the eyes (ce), closing the eyes forcefully (cef), grinding the teeth (gt), clearing the throat (clt), saliva noise (sn), coughing (c), and talking (t). Understandably, the present disclosure is not limited to the above-mentioned nonverbal audio events as any other nonverbal audio event producing an audio signal in the ear-canal may be characterized.

It shall be recognized that any number of suitable audio features can be extracted and stored in the audio feature database 16 and the type of audio features to extract can vary from one application to another depending on the nonverbal audio events to store.

It shall further be recognized that the audio feature database 16 can be part of the event classification module 19 and can be replaced by an executable code, without departing from the present classification system 10.

According to one embodiment, the association may be performed manually. In other embodiments, the association may be performed by any suitable computer-implement classification method used to at least partially analyze or extract audio features and adequately classify or categorized the various nonverbal audio events based on a variety of audio features or acoustic properties, such as frequency, volume, loudness, length etc.

In some embodiments, the nonverbal audio events are classified in the database 16 using the Mel-Frequency Cepstral Coefficients (MFCCs) and auditory-inspired amplitude modulation features (AAMFs) as classifying audio features.

In one example, thirteen MFCCs may be computed for each 50 ms frame with a 50% overlap. In such case, each audio feature vector consists of 13 MFCCs, delta, and delta-delta coefficients resulting in a 39-dimension feature vector for each of the 30 captures frames.

The zero-rate crossing is also calculated for the 400 ms sample and added to the overall feature vector. For classification, any machine learning algorithm may be used such as support vector machine (SVM), Gaussian Mixture Models (GMM), Bag of audio words (BoAW) and a Multi-Layer Perception (MLP) neural network. The parameters of each of the machine learning algorithms are chosen to obtain a desired level of overall accuracy of the model over all or a desired range of classes.

According one embodiment, audio signals are captured from a group of people and the extracted audio feature values are stored in the audio feature database 16 in various forms. For instance, in one case an average of each of the extracted audio feature values are stored in the database 16. In another case, a range of extracted audio feature values are stored in the database 16. In another case, a statistical probability factor is associated to each extracted audio feature value. In yet another case each extracted audio feature value are stored in the database 16 according to at least one person related attribute such as age, weight, height, sex, nationality, etc.

Figure 3:
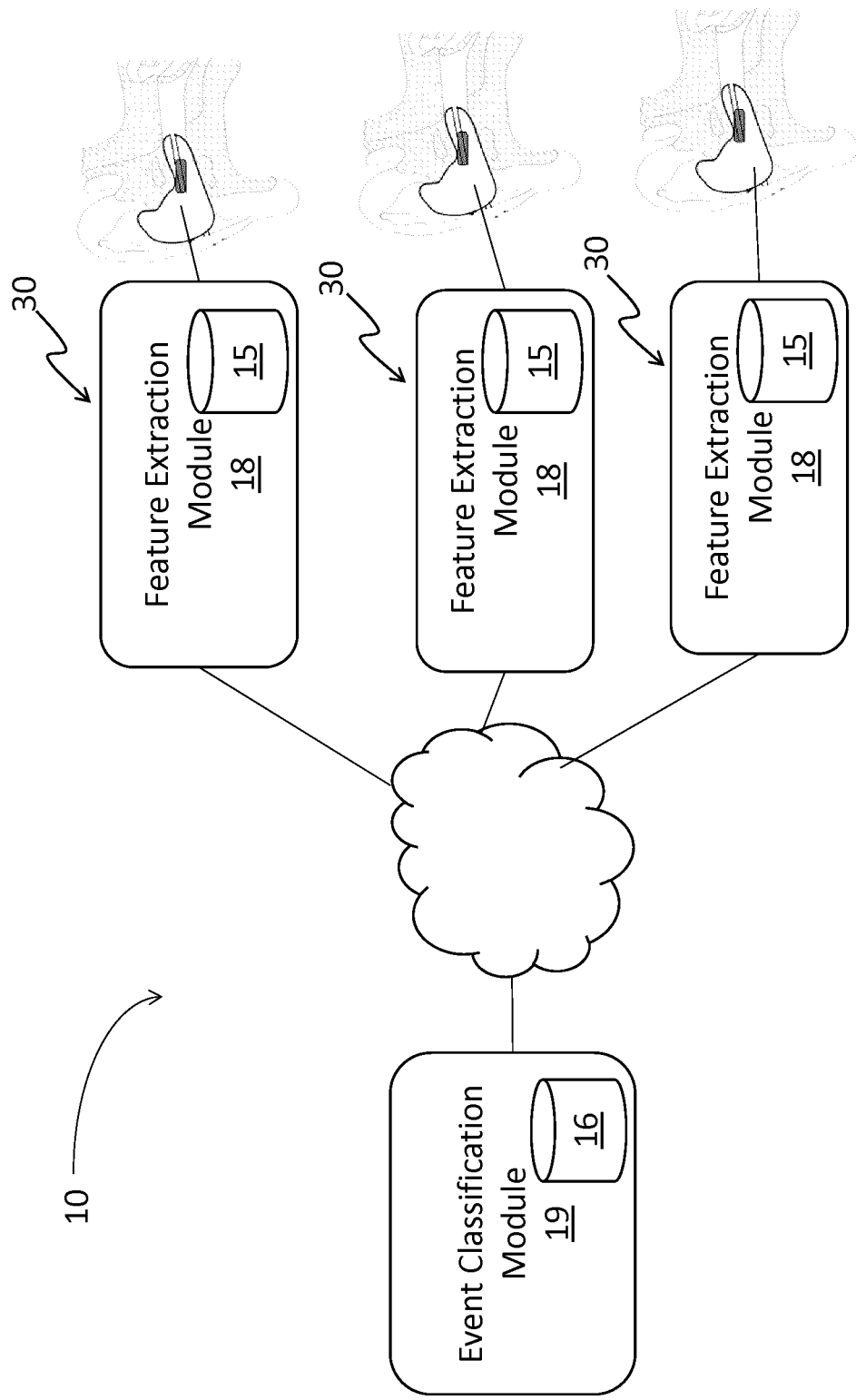
FIG. 3 is a diagram showing an embodiment of a system for training a classification module of nonverbal audio events by capturing in-ear audio signals and using a plurality of audio feature extraction modules in accordance with one embodiment.

It shall be recognized that as presented in FIG. 3, nonverbal audio event feature values can be extracted by remote devices 30.

Figure 4:
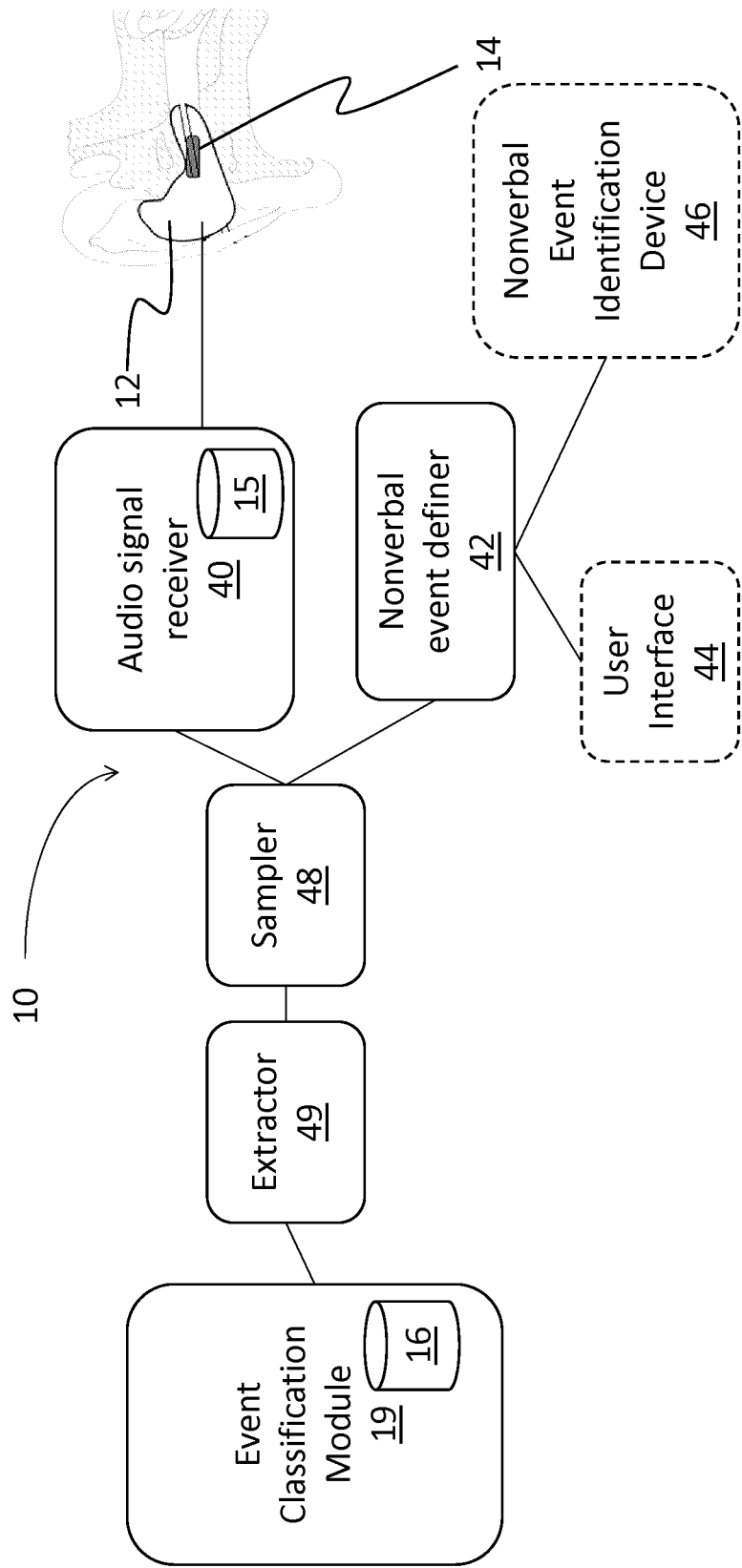
FIG. 4 is a diagram showing an embodiment of a system having an event definer for training a classification module of nonverbal events captured as in-ear audio signals, in accordance with one embodiment.

According to one embodiment as presented in FIG. 4, the audio feature extraction module 18 may comprise an audio signal receiver 40, a nonverbal audio event definer 42, a sampler 48 and an extractor 49. The audio signal receiver 40 is adapted to receive a captured audio signal from the microphone 14. The nonverbal audio event definer 42 is configured to receive a nonverbal audio event definition to be associated with the captured audio signal from either a user interface module 44 or from a nonverbal audio event identification device 46. The user interface 44 is adapted to receive a nonverbal audio event information from a user such as the wearer or another person. The nonverbal audio event identification device 46 is adapted to identify the nonverbal audio event with another method such as with an audio signal filtering method, with another nonverbal audio event identification module or with another populated database.

The sampler 48 receives the audio signal from the receiver 40 and samples the audio signal according to a predetermined sampling rate or according to a sampling rate associated to the defined nonverbal audio event received from the definer 42. For instance, audio signal samples of 400 ms are extracted for each nonverbal audio event. It shall be recognized that the samples may be of any required length and can vary depending on the type of nonverbal audio event, available storage space, required level of accuracy, number of nonverbal audio events to classify, etc.

An extractor 49 then receives the sampled audio signal and extracts the values corresponding to a predetermined group of audio features or the values of a group of audio features corresponding to the defined nonverbal audio event as provided by the nonverbal audio event definer 42. The extracted audio feature values are then stored in the database 16 in association with the defined nonverbal audio event by the audio feature association module 19.

It shall be recognized that in comparison with single ear intra-aural recording, recording of audio signals captured in both occluded ear canals of a user, also known as Binaural recording, generally aims at enhancing the efficiency of the classification method and at increasing the accuracy of event detection since a greater amount of data can be stored in the database 16.

Training the Event Classification Module

According to one embodiment, the event classification module 19 is trained by a machine learning algorithm as new extracted audio features are being provided by the audio feature extraction module 18. The audio feature extraction module 18 is adapted to provide new extracted audio features for a same nonverbal audio event, based on previously captured signals that are stored in the signal database 15 or based on a different sample of a same captured signal that is stored in the signal database 15.

In one embodiment, the audio feature association module 19 is trained with an SVM machine learning algorithm. A one-vs.-all classifier is used with a linear kernel to compute 11 hyperplanes needed for the classification of nonverbal audio events.

In another embodiments, the audio feature association module 19 may be trained with a GMM machine learning algorithm used with a diagonal covariance matrix. The matrix typically comprises 11 classes and 15 Gaussians per class, for a total of 165 Gaussians.

In another embodiment, the audio feature association module 19 is trained with a BoAW machine learning algorithm used with a clustering algorithm, such as the GMM algorithm with 15 gaussians per class, and with a classifier, such as the SVM algorithm with a C of 0.1.

In yet another embodiment, the audio feature association module 19 is trained with a MLP machine learning algorithm. Three hidden layers with a rectified linear activation function and a linear activation function for the output layer are used. The network is trained using the cross entropy loss function and the Adam method of optimization.

It shall be recognized that a combination of classifiers can be used by applying a fusion scheme of different classifiers for a variety of classes in order to increase the accuracy of the trained audio feature association module 19.

Figure 5:
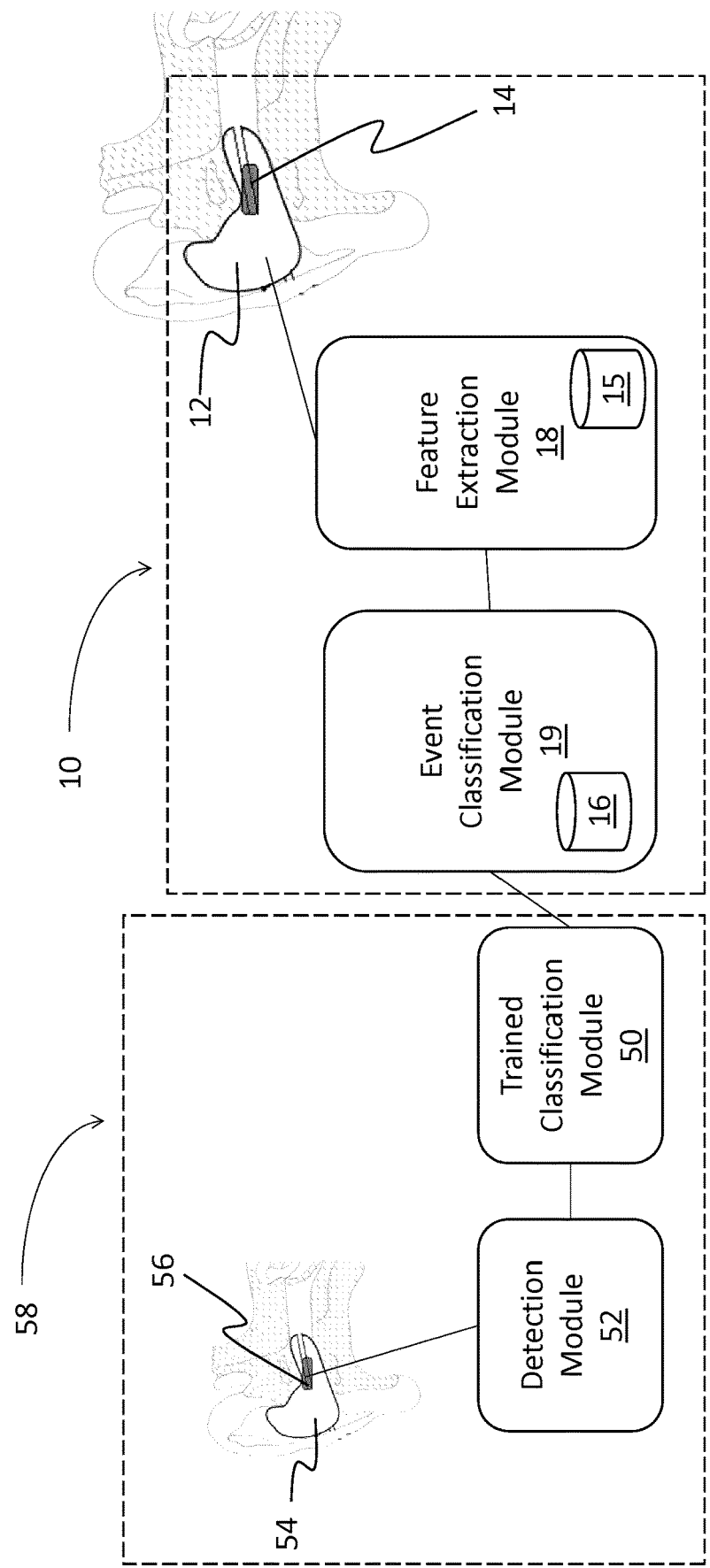
FIG. 5 is a diagram of the system for training a classification module of FIG. 1 and of a system for detecting a nonverbal audio event from a captured in-ear audio signal by using the trained classification module, in accordance with one embodiment.

Once adequately populated, either the database 16 or the event classification module 19 is used to program or train a nonverbal audio event classification module 50, as presented in FIG. 5. Notice that the trained classification module 50 can be a copy of the event classification module 19. The trained classification module 50 can be installed or accessed by a nonverbal audio event detection module 52 for detecting nonverbal audio events from audio signals that have been captured with another intra-aural device 54 positioned in an occluded ear or in a non-occluded ear. Understandably, in other embodiments, the database 16 and the event classification module 19 may be partially used to train the module 50.

The training of the classification module may be performed using any relevant machine learning techniques or methods. As an example, the training may generate a script or binary instructions configured to efficiently perform a live or real-time classification method integrating the audio signals features used to train the classification module 50. In typical embodiments, the trained classification module 50 in operation does not rely on the database 16 or the classification module 19.

According to one embodiment, the detected event by the detection module 52 is used by another device or module for correlation purposes. For instance, the detected event may be correlated with another detected event that has been captured by a biosensor device. In such example, an output is produced according to the correlated result. In yet other embodiments, the detected event can also be interpreted by another module to produce an output such as a command output, a detected event output, an event measurement output, etc.

Figure 6:
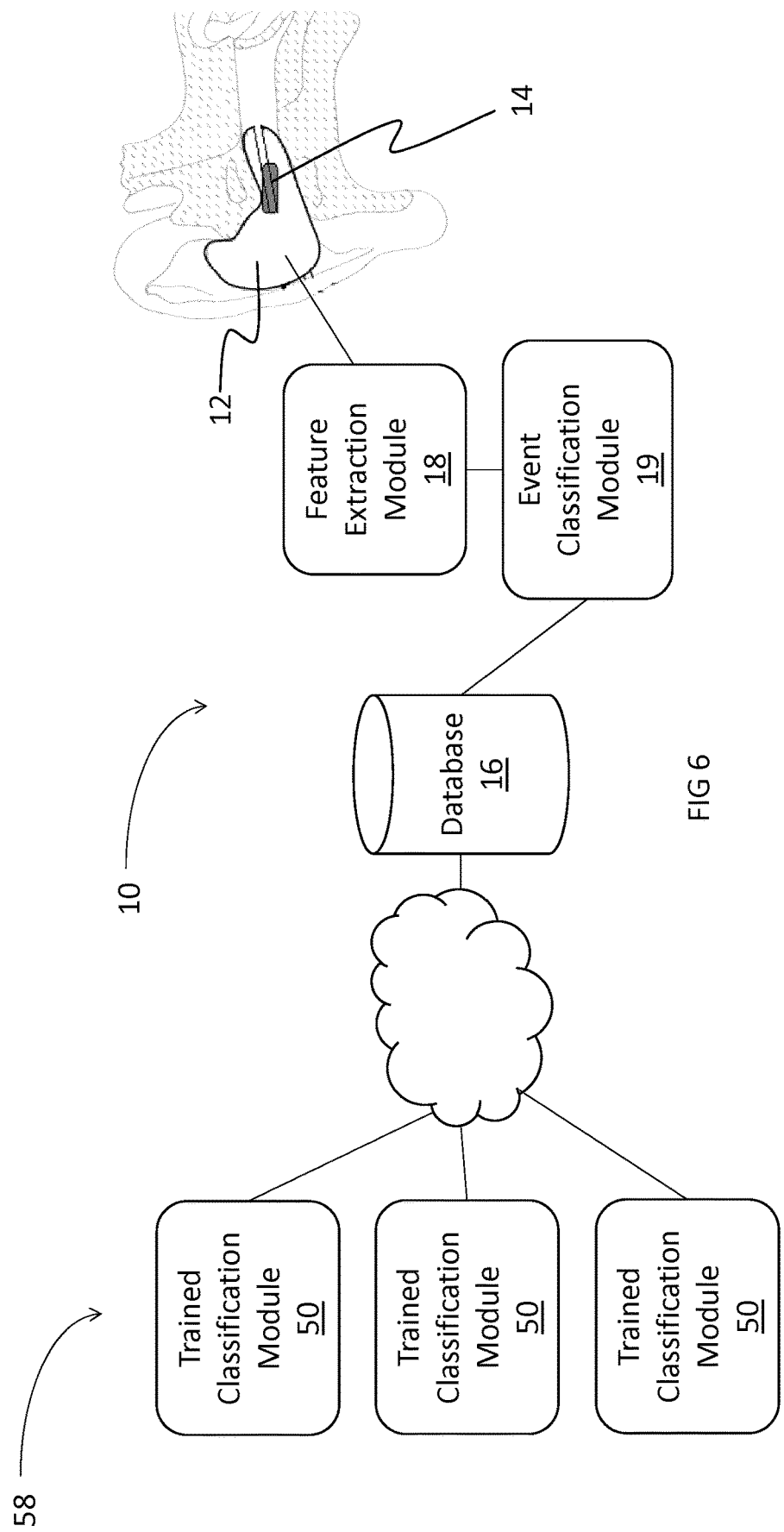
FIG. 6 is a diagram of a plurality of classification modules trained with the system of FIG. 1, in accordance with one embodiment.

As presented in FIG. 6, according to one embodiment, the database 16 is used to program or train a plurality of classification modules 50 that are either directly connected to the database 16 or remotely connected to the database 16. Notice that the classification modules may have been previously trained by another database or by the same database and can be updated according to any new data that is stored in the database 16.

Figure 7:
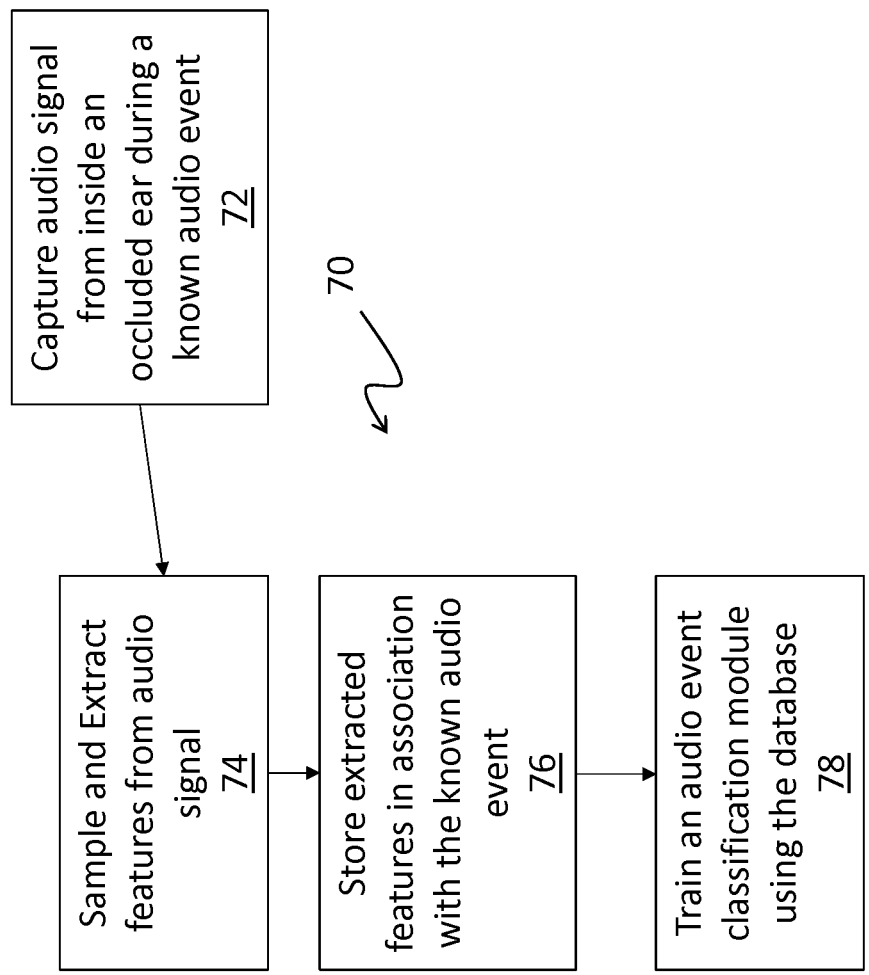
FIG. 7 is a block diagram of a method for training or producing a nonverbal audio event classification module by capturing audio signals from an occluded ear canal, in accordance with one embodiment.

Method of Producing the Trained Classification Module for Detecting a Non-Verbal Event Presented in FIG. 7 is a method 70 of producing the trained classification module 50 with a database 16 having extracted audio features of relevant captured audio signals associated to a known nonverbal audio event. According to one embodiment, the method 70 captures audio signals from inside an occluded ear 72. The audio signals are sampled and processed to extract audio features 74, those extracted audio features are stored 76 in a database 16 in association with the known nonverbal audio event. The database 16 is used for training 78 the audio event classification module 50. The database can also be used for testing or updating the trained audio event classification module 50, as concurrently presented in FIG. 5.

Figure 8:
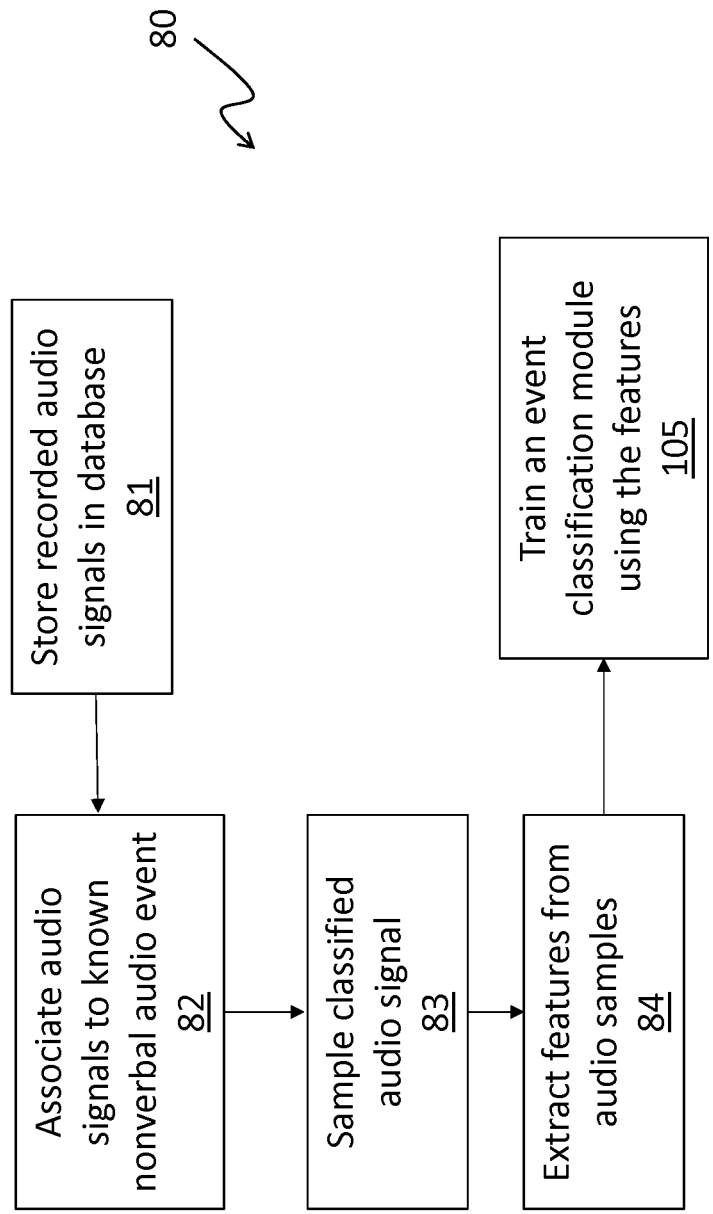
FIG. 8 is a block diagram of a method for training or producing a nonverbal audio event classification module by capturing audio signals from an occluded ear canal, in accordance another embodiment.

According to another embodiment, as presented in FIG. 8, there is a method 80 for training the classification module (19 or 50), as concurrently presented in FIG. 5. The method 80 comprises storing, creating or building a directory of recorded or captured audio signals indicative of or associated to nonverbal audio events 81. The captured audio signals may be stored in any data source, such as, but not limited to the database 15, a binary file or any file system, as concurrently presented in FIG. 1. The captured audio signals may also be stored using any type of media, such as any audio format.

The method 80 further comprises associating 82 the nonverbal audio signals to a known nonverbal audio event, in the database 15. As presented in FIG. 10 according to one embodiment, the associating step 82 is performed manually 102 to distinguish the different types of audio signals, such as but not limited to clicking of teeth softly (cts), clicking of teeth loudly (ctl), tongue clicking (cl), blinking forcefully (bf), closing the eyes (ce), closing the eyes forcefully (cef), grinding the teeth (gt), clearing the throat (clt), saliva noise (sn), coughing (c), talking (t), moving body or head (bo), yawning (inspiration) (ba1) and/or yawning (expiration) (ba2). Thus, each captured audio signal is associated with one or more known nonverbal audio event. In other cases, an association process could be executed to at least partially associate or pre-associate the audio signals automatically or semi-automatically.

The method 80 may further comprise sampling the classified audio signals 83. In some embodiments, as presented in FIG. 10, the audio signals are sampled as 400 ms segments 103. A 400 ms segment is typically adequate for a variety of nonverbal audio events produced by a human such as blinking, throat clearing events as well as teeth clicking and tongue clicking events that are known to have a relatively shorter duration than blinking and throat clearing. However, as a yawning event typically lasts longer than 400 ms, it is preferable to divide such an event into more than one segment (such as inspiration and expiration, in the case of a breathing event). Understandably, any suitable sampling length or method may be used without departing from the scope of the present disclosure. Also, it shall be recognized that the sampling length can vary depending on the type of nonverbal audio event.

The method 80 further comprises extracting audio features from the audio samples 84. For instance, as presented in FIG. 10, MFCCs can be extracted from the audio samples 104. The MFCCs are coefficients of the audio energy at different frequency ranges or bandwidths. Such ranges are normalized and have a relative weight adapted to the human perception of the sounds. To transform the audio samples to MFCCs, any programming language used for signal processing such as Matlab, Python, C, etc. can be used, compiled and executed. Other audio features may comprise the delta and acceleration of the samples. Preferably, the values associated with each audio feature are inserted in a vector to be used with classifiers, such as SVM and GMM.

Figure 10:
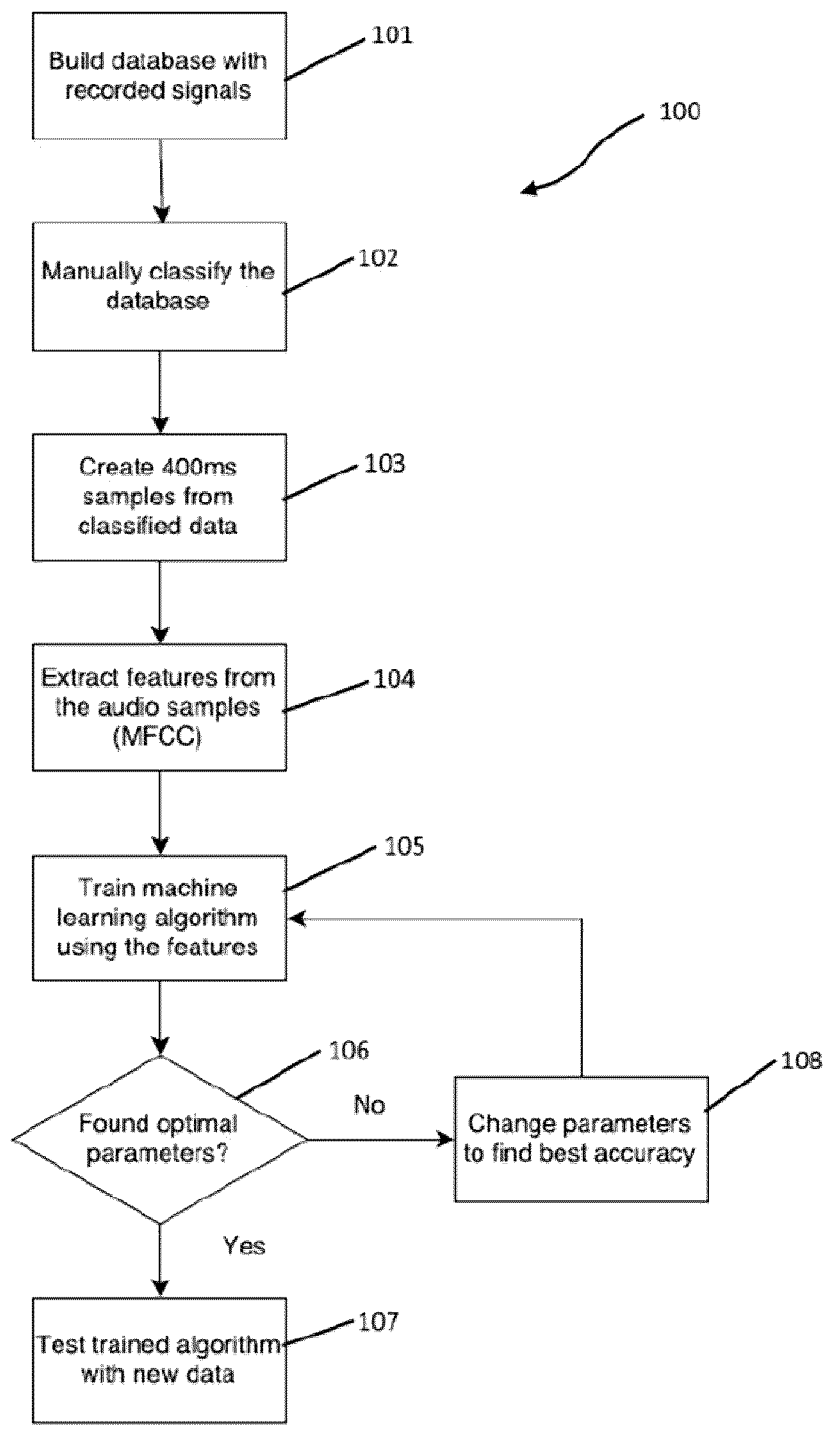
FIG. 10 is a block diagram of a method for training or producing a classification module according to the method of FIG. 8, according to one embodiment.

The method 80 further comprises training 85 an event classification module with a machine learning algorithm 105 by using the extracted audio features, as concurrently presented in FIG. 10. The event classification module (19 or 50) can be trained by any suitable type of machine learning algorithm, such as SVM, GMM or MLP. The SVM algorithm allows division of the data using a hyper-plane, without being limited by the number of dimensions of the samples. In one embodiment, the sklearn library is used with modules SVC and OneVsRestClassifier. For instance, a LinearSVC having a C constant of 0.007 is used.

Figure 9:
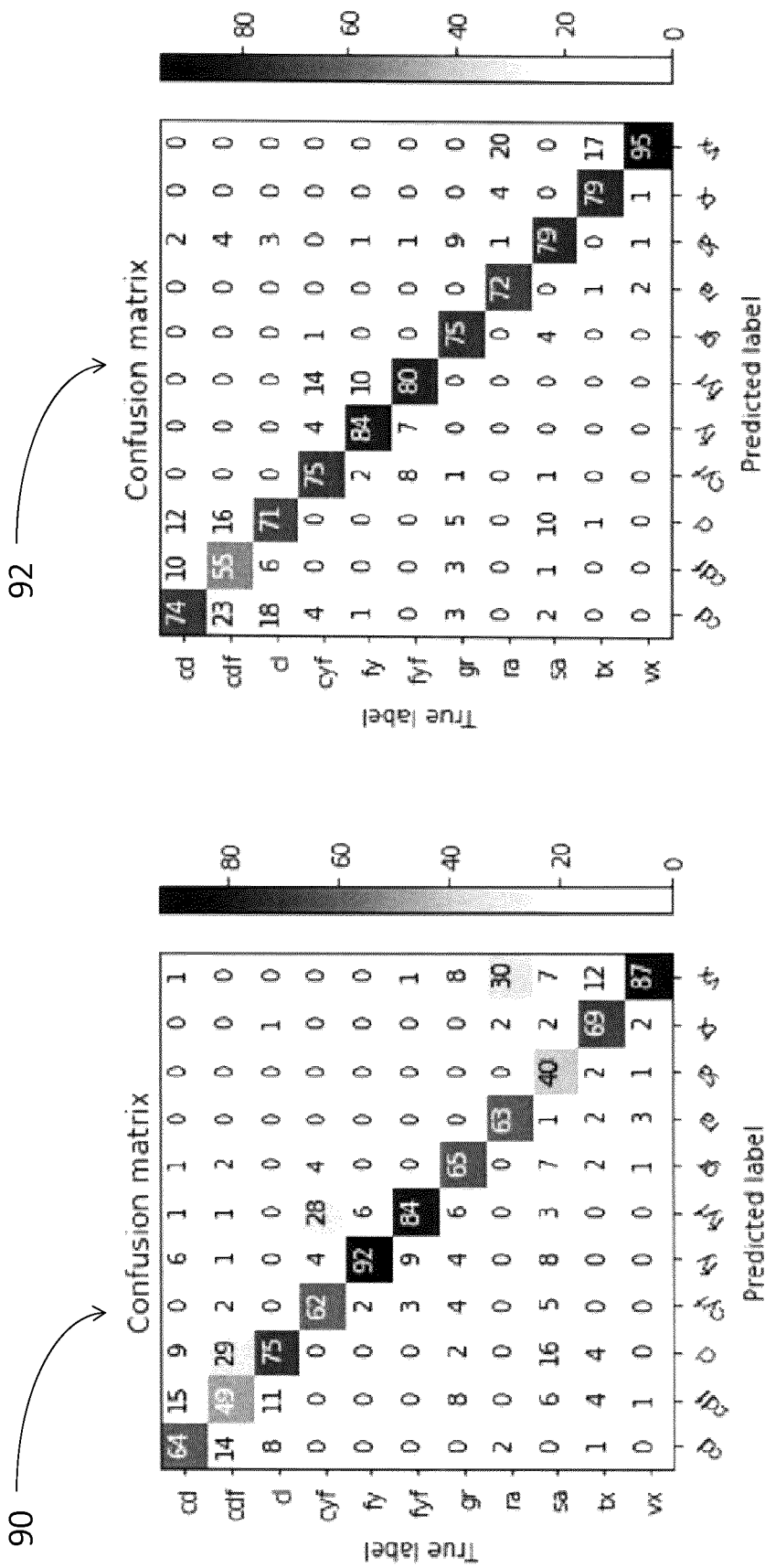
FIG. 9 is a resulting confusion matrix using a support vector machine (SVM) training algorithm and a resulting confusion matrix using Gaussian Mixture Models (GMM), according to one embodiment.

A resulting confusion matrix 90 using SVM is shown at FIG. 9. In another embodiment, the GMM algorithm is used to train the classification module using Gaussians to show data span of a specific class. For instance, a mix of 6 Gaussians may be used per class. A resulting confusion matrix 92 using GMM is further shown at FIG. 9.

According to one embodiment, the BoAW algorithm is used to train the event classification module using Gaussians to cluster the data and create a wordbook. In a typical example, a wordbook of size 165 is used to represent 11 classes. This wordbook is used to create a histogram of the clusters activated by each sample. This histogram is classified using an SVM with a constant C of 0.1. Different features such as MFCC or AAMF can have their own codebook and histogram. Their histograms can then be concatenated together to have more information about the sample and then classified.

As presented in FIG. 10, following the training 105 of the event classification module (19 or 50), the method 100 may validate if the parameters of the event classification module have a desirable level of accuracy 106. The desired level of accuracy is generally determined by the number of true positive outcomes.

If the method 100 determines that the parameters are optimal 106, the trained algorithm is tested 107 using a new audio signal that has not been used during the training 105, such as new audio signals captures by intra-aural devices. If the method 100 determines that the parameters are not optimal 106, the parameters are modified 108 and the event classification module is trained once again using the modified parameters 105.

Figure 11:
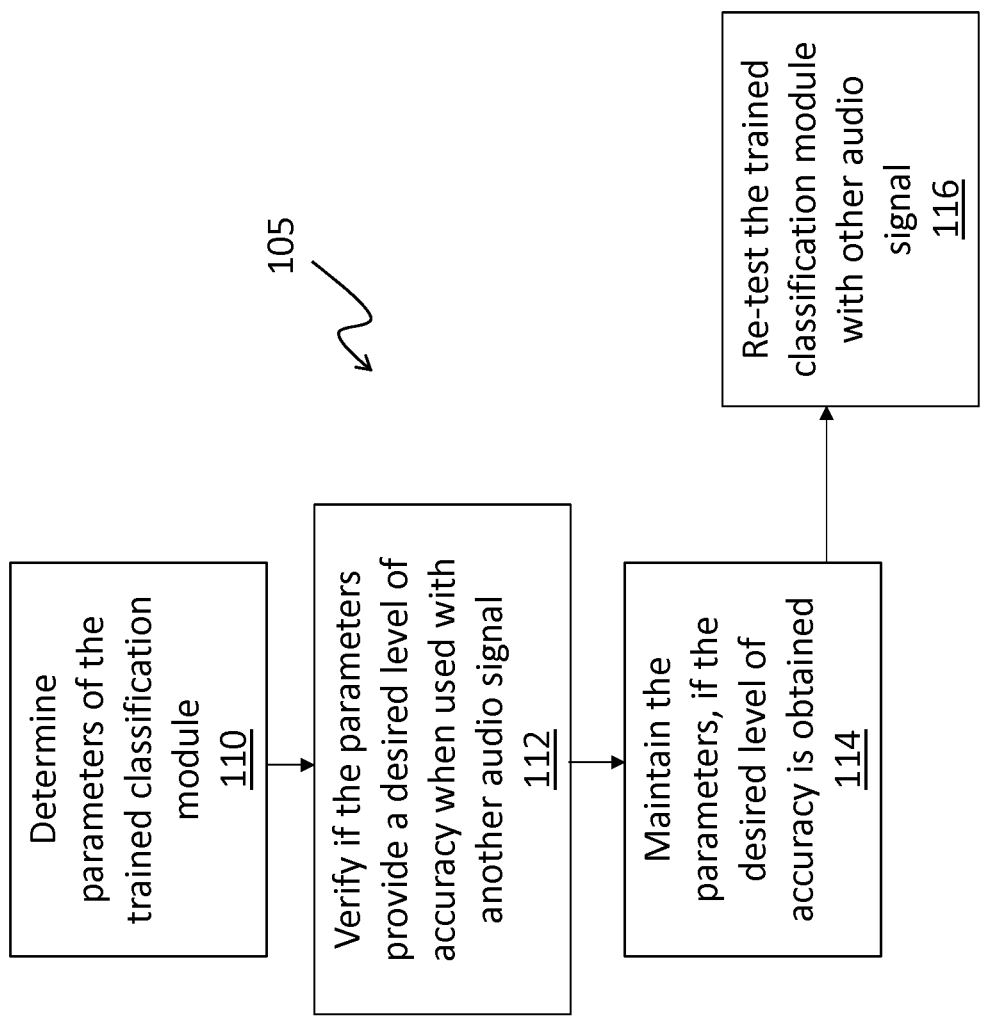
FIG. 11 is a block diagram of a method for training or producing an event classification module using the extracted audio features from an audio sample, according to one embodiment.

In an alternate embodiment, as presented in FIG. 11, there is a method of training classification module 105. The method 105 determines a first group of parameters for the classification module 110. Then, the parameters are validated by verifying 112 if a desired level of accuracy is reached when used with another audio signal or audio signal sample for the same nonverbal audio event. If the desired level of accuracy is reached, the determined group of parameters are maintained 114. The trained classification module can be re-tested 116 with other audio signal or audio signal samples, as necessary.

In one embodiment, the classification module (19 or 50) is trained by the intra-aural device of the user. In such an embodiment, the user identifies the various events using a device such as a smart phone or a computer to train or retrain the event classification module (19 or 50).

In another embodiment, the device could use other sensors such as a gyroscope and/or accelerometer, temperature, humidity, blood pressure and flow (PPS), to confirm or validate an adequate training of the event classification module 19 or the trained classification module 50.

Once adequately trained, as further presented in FIG. 5, the trained classification module (19 or 50) can be installed in detection or monitoring modules 52 of various intra-aural devices 54 having an in-ear microphone 56. According to one embodiment, the trained classification module (19 or 50) is pre-installed on the intra-aural device 54 and allows a user to detect nonverbal audio events coming from his or her body.

Notice that the classification module (19 or 50) can be retrained as often as necessary or even on a continuous basis during a prolonged period of time in order to perfect the parameter accuracy of the classification module and also to adapt the parameters specifically to a given user or group of users. It is understood that individual anatomy, personality and genetics may lead to a broad range of audio signals for a specific nonverbal event. This can lead to low accuracy in classification and can impede effectiveness in various applications. To alleviate this issue, a system that starts from a generic baseline, can be trained over time to learn each user's individual representation of each class over time and ultimately yield to a better performing classifier.

For instance, an initial version of the classification module (19 or 50) provided by a manufacturer can be deployed or installed on a nonverbal detection module. The initial version of the classification module (19 or 50) is suitably trained with a group of generic audio signals by the manufacturer, however, the module (19 or 50) might still require some adjustments for a particular user. Once acquired by the user, the classification module (19 or 50) can be retrained to make the necessary adjustments. The retraining of the classification module (19 or 50) can be triggered by the user or can be produced automatically, depending on the area of application and tuning requirement. Moreover, the retraining of the classification module (19 or 50) can be produced according to classification module parameters provided by other users of a same group.

Figure 12:
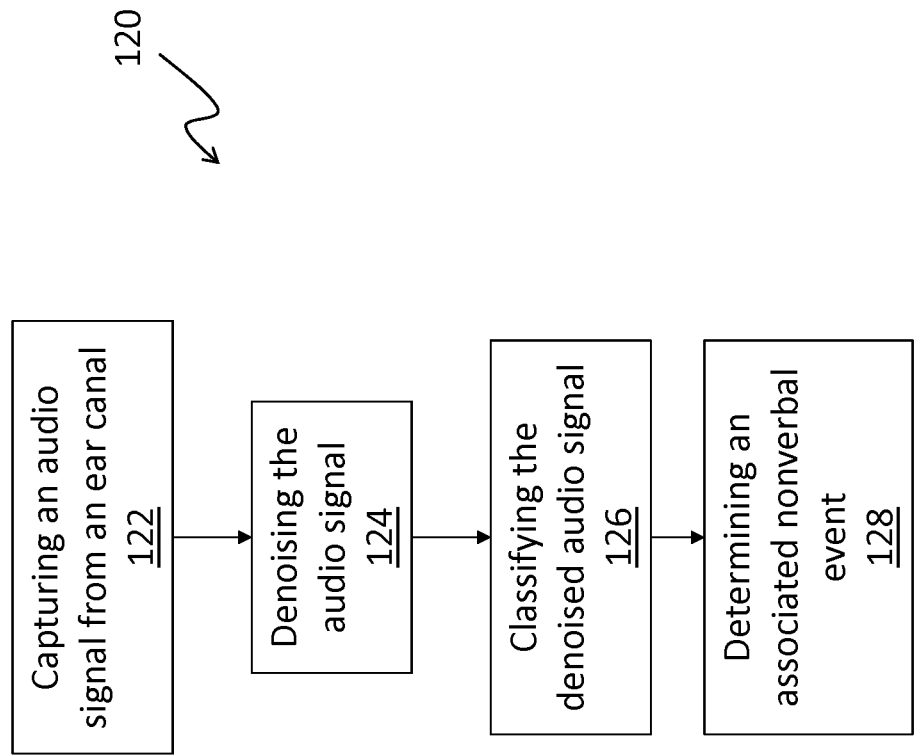
FIG. 12 is a block diagram of a method for determining a nonverbal audio event from a captured audio signal in an ear canal, according to an embodiment.

According to one embodiment, as presented in FIG. 12, there is a method 120 of detecting a nonverbal audio event with the detection or monitoring module 52 having the trained classification module (19 or 50). The method 120 captures an audio signal from the ear canal with the in-ear microphone 56. The captured audio signal is denoised 124 and the denoised signal is classified 126 with the classification module (19 or 50). Once classified, the detection or monitoring module 52 determines 128 the associated nonverbal audio event according to the classification. Indeed, there is no need to resort to filtering methods that are time consuming and require extensive processing power especially in real time applications. The classification module (19 or 50) is trained with the right parameters to accurately and practically instantaneously classify the captured audio signal, such that a detection module or monitoring module can identify from inaudible audio signals captured within the ear canal, an extensive number of nonverbal audio events.

Various Applications Using Trained Classification Module

Figure 13:
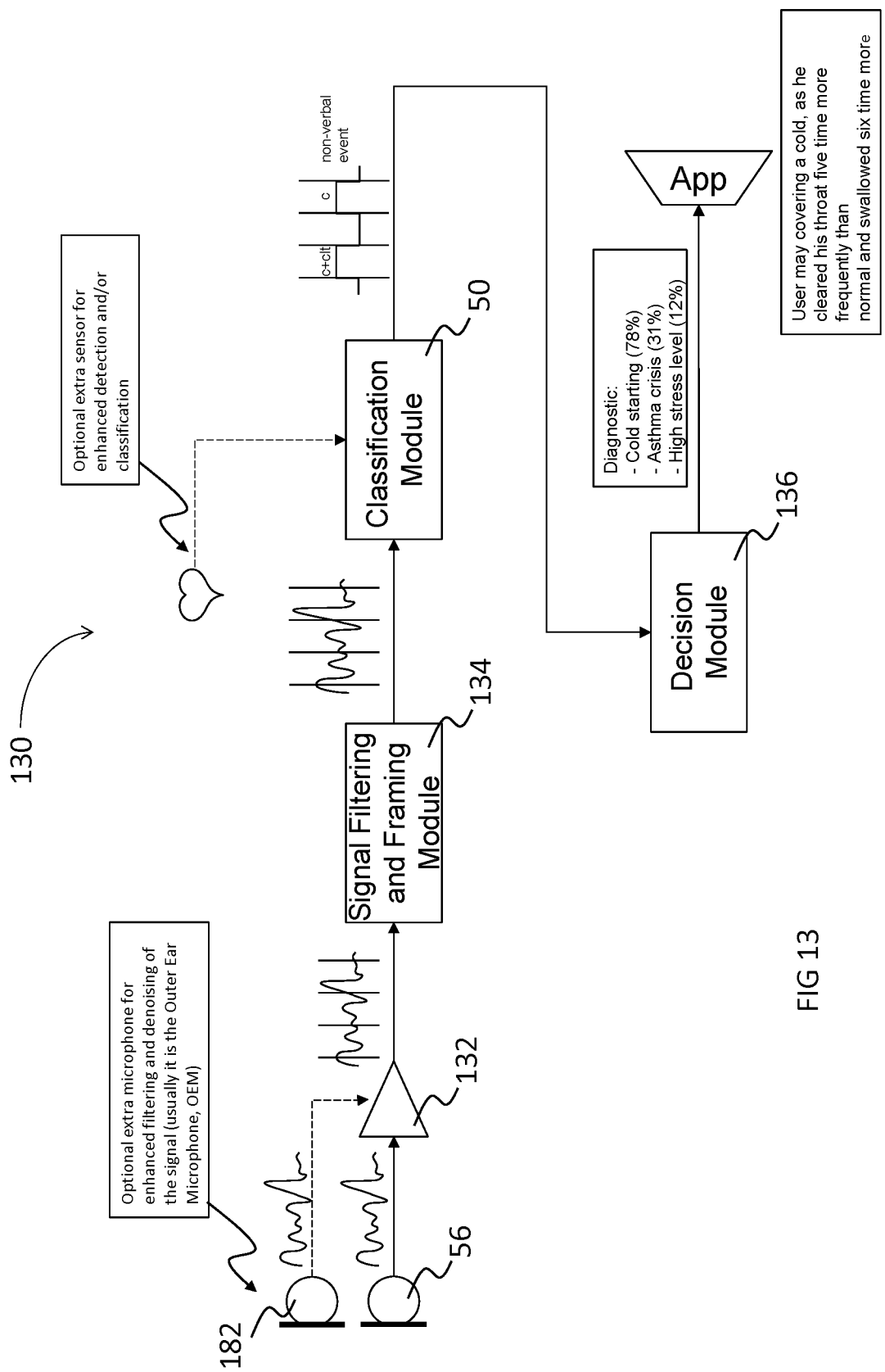
FIG. 13 is a block diagram of a health and mood monitoring system having the trained classification module of FIG. 5, according to one embodiment.
Figure 14:
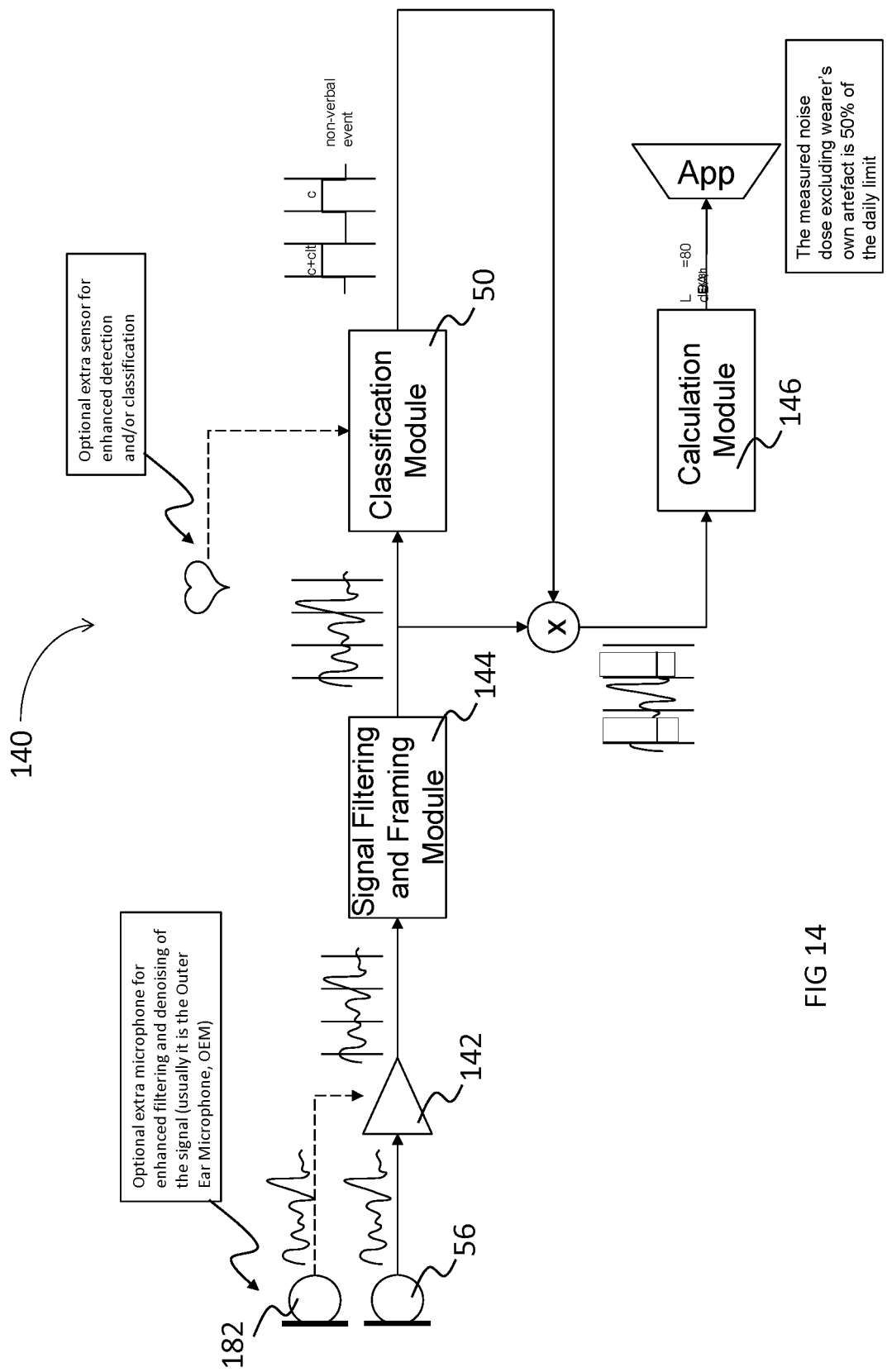
FIG. 14 is a block diagram of an in-ear noise dose measurement system adapted to remove artefacts with the trained classification module of FIG. 5, according to one embodiment.
Figure 15:
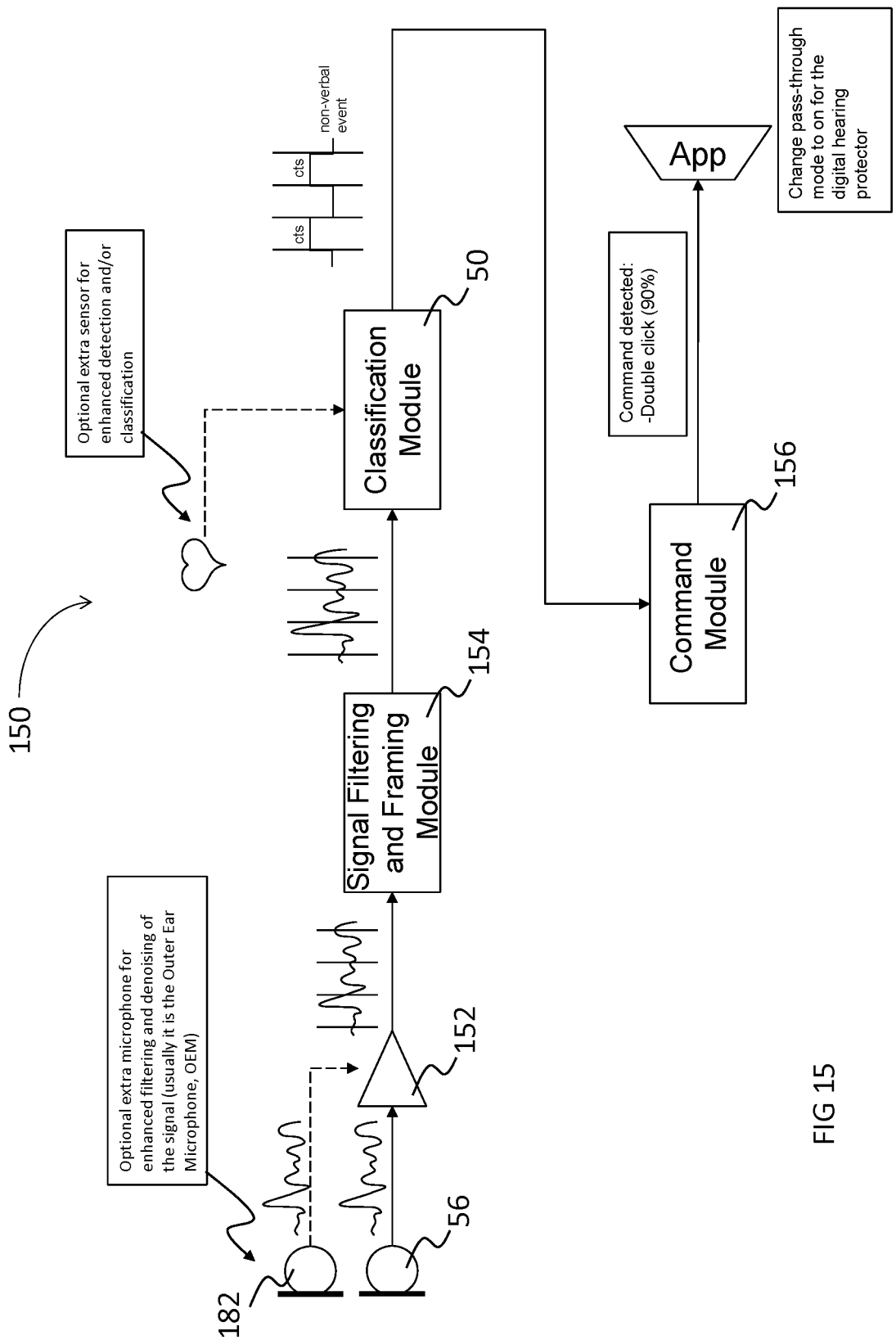
FIG. 15 is a block diagram of a silent interface and assistive system having the trained classification module of FIG. 5, according to one embodiment.
Figure 16:
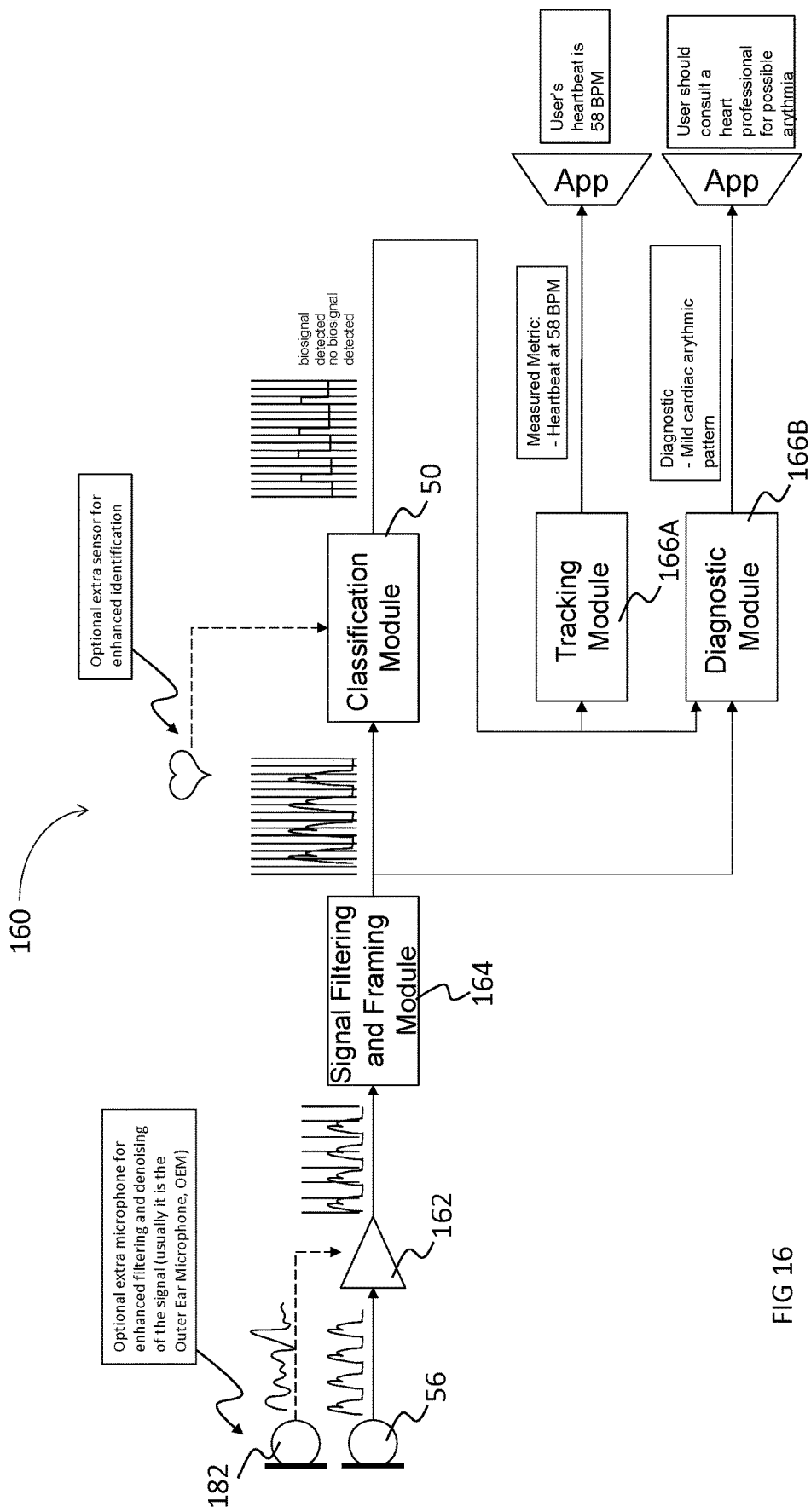
FIG. 16 is a block diagram of a biosignal monitoring system having the trained classification module of FIG. 5, according to one embodiment.
Figure 17A:
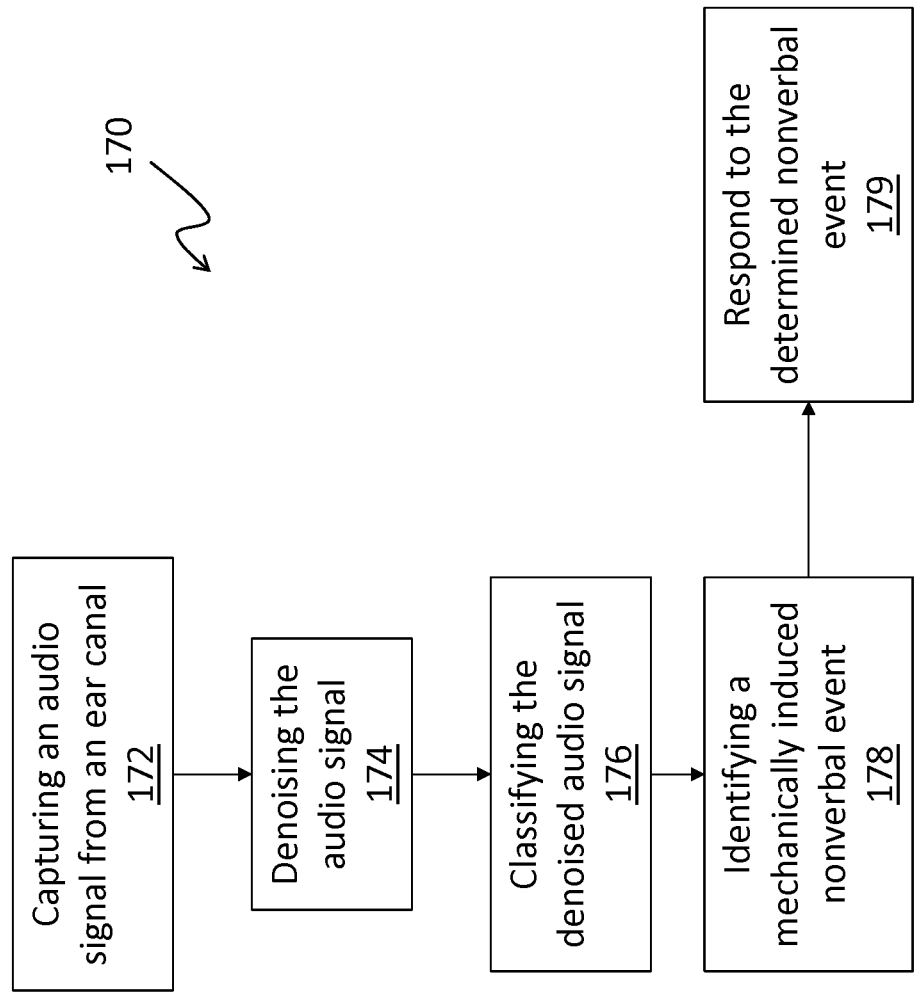
FIG. 17A is a block diagram of a method for detecting a mechanically-induced nonverbal audio event, by classifying a captured in-ear audio signal associated to the nonverbal audio event, according to one embodiment.
Figure 17B:
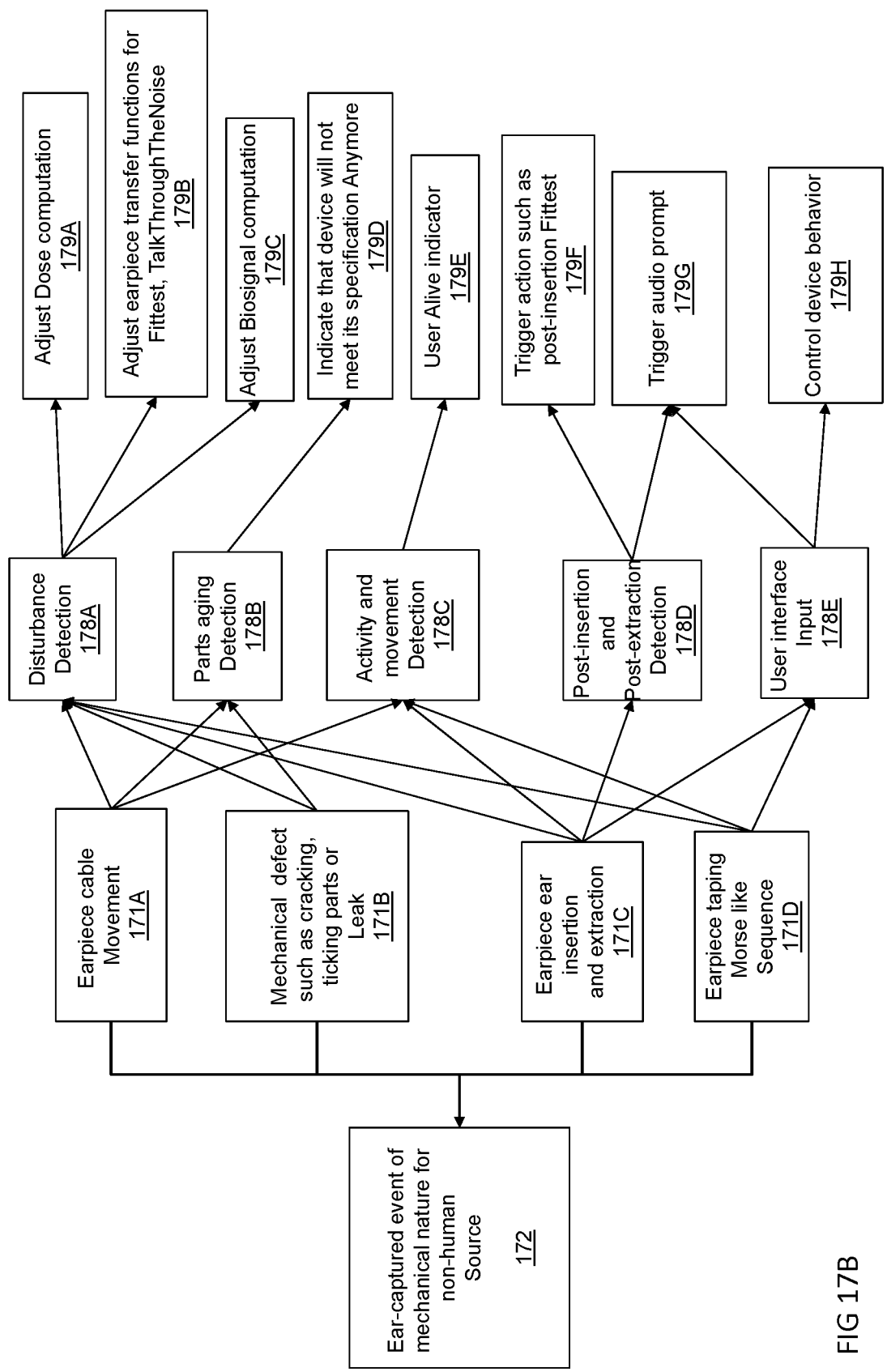
FIG. 17B is a block diagram of possible mechanically-induced nonverbal audio events and associated possible responses as provided by the method of FIG. 17B, according to one embodiment.
Figure 18:
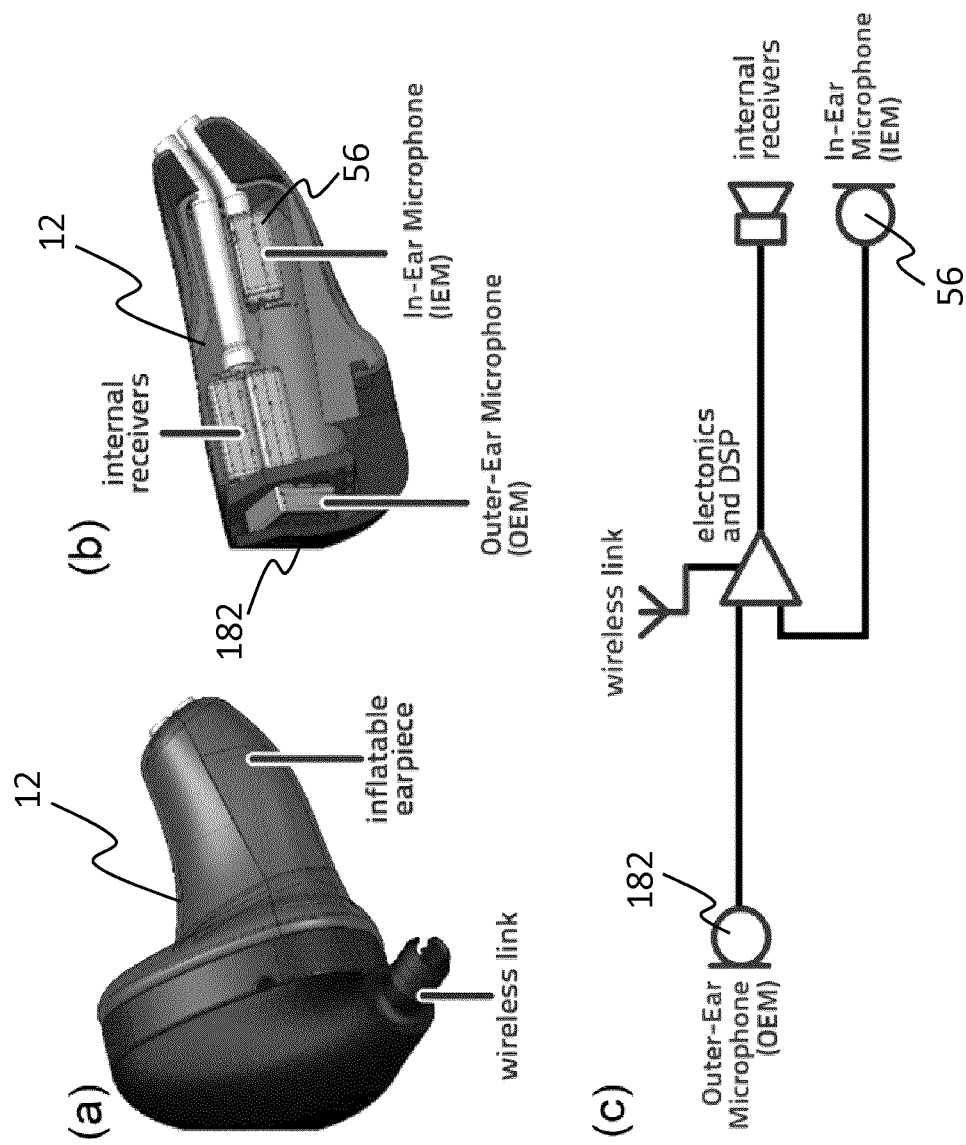
FIG. 18 is a schematic view of an electronic wearable in-ear device for capturing an in-ear audio signal and detecting a nonverbal audio event as provided by the systems of FIGS. 13 to 16, according to one embodiment.

The accurate classification of such audio signals allows to perform or perfect diverse detection applications such as health and mood monitoring applications as presented in FIG. 13, artefact removal applications as presented in FIG. 14, silent interface and assistive applications as presented in FIG. 15, biosignal monitoring applications as presented in FIG. 16 and Detection of mechanically-induced sound events as presented in FIGS. 17A and 17B, etc. Understandably, such applications are illustrated as examples only, a trained classification module may be used in any other applications and in any fields of applicable.

As presented in FIG. 13, the trained classification module (19 or 50) allows to accurately and rapidly identify a variety of nonverbal audio events produced by the human body in order to monitor the general health of an individual or track symptomatic effects of a given pathology. For instance, nonverbal audio events such as throat clearing, coughing, yawning, etc. can be used for general health monitoring and/or fatigue of an individual. By properly monitoring the occurrence rate of such events, an assessment can be made of a health condition, relative to the individual wearer or to normative data obtained on a group of people. The audio signals captured inside the ear canal can be symptomatic of an appearing, established and disappearing disease, ailment (a cold, etc.) or sickness (asthma, etc.), a level of tiredness, etc. Also, some other nonverbal audio events (such as teeth grinding, frequent swallowing, etc.) can be symptomatic of a given stress level or mood state.

Still referring to FIG. 13, general health monitoring system and method 130 are illustrated. The system 130 has an in-ear microphone 56 or pressure sensor, such as presented in FIG. 5, located inside the ear canal or at the vicinity of the ear canal and that measures the sounds present in the open or occluded human ear-canal. The signal captured by the in-ear microphone 56, such as an electric signal, is sent to an analog to digital converter 132 (ADC) that outputs signal time frames of equal duration. It shall be noted that the ADC 132 can be part of or integrated in the microphone 56, or part of a signal processing unit. Understandably, in other embodiments, the in-ear microphone 56 could also directly output a digital signal.

The system 130 further comprises various signal processing modules adapted to process the signal time frames. The signal processing modules typically comprise a signal filtering module 134, the trained classification module 50 and a decision module 136. In a typical embodiment, the signal time frames are first handled by the filtering module 134. The filtering module 134 generally performs the proper time or frequency filtering required to enhance the signal-to-noise ratio of the incoming signal. The filtering module 134 can take into consideration a second signal captured by microphone or pressure sensor, such as an Outer Ear Microphone 182. In a typical embodiment, the Outer Ear Microphone 182 is positioned at an outer faceplate of the in-ear device 160, as concurrently presented in FIG. 16. The trained classification module (19 or 50) receives the filtered signal time frames and verifies or validates if the captured signal is a nonverbal audio event. If the captured signal is a nonverbal audio event, the trained classification module (19 or 50) attempts to accurately identify the nonverbal audio event according to adjusted audio feature parameters. The output of the trained classification module (19 or 50) is a value that uniquely identifies the one or many nonverbal audio events. The decision module 136 then receives the identified nonverbal audio event and performs required statistical analysis to provide an assessment of a condition such as a health condition, emotional condition, etc. The assessed condition is then presented to the user or sent to another monitoring device.

Now referring to FIG. 14, an embodiment of an artefact removal system 140 is illustrated. The artefact removal system 140 can be used for instance with in-ear noise dose measurement. In-ear dosimetry is performed to ensure safety and avoid noise-induced hearing loss, such as by workers in noisy environments that are usually equipped with hearing protection devices. In such environment, a noise dosimeter is used to calculate an individual's exposure to noise during his work day.

However, one of the drawbacks of in-ear dosimetry is that user-generated disturbances such as clearing the throat, speaking or coughing events are not distinguishable from environmental noise and are considered when calculating the accumulated noise dose. In fact, such user-generated disturbances can generate large sound pressure levels that are not necessarily relevant for the dosimetry measurement and should be discarded from the noise dose calculated. Such user-generated disturbances do not induce hearing damage, a natural protection mechanism is believed to occur and the user cannot be affected by the sound of his own sneezing. However, to an untrained dosimeter, the levels of noise or sound inside the ear caused by nonverbal audio events produced by the user can be mistakenly added to the dose calculation. Such erroneous addition to the dose calculation may lead to inaccurate dosimetry readings at the end of the workday. Therefore, the ability to accurately detect and reject physiological noises with the audio event classification module allows to calculate the worker's noise exposure with greater accuracy.

Still referring to FIG. 14, an embodiment of in-ear noise dose measurement system and method 140 adapted to accurately remove unwanted artefacts is shown. The system 140 generally comprises an in-ear microphone 56 or pressure sensor, conveniently located inside the ear-canal or in the vicinity of the ear-canal. The in-ear microphone 56 is configured to capture the sounds present in the open or occluded human ear-canal, such as concurrently presented in FIG. 5. The captured signal is converted to a digital signal by an ADC 142 that outputs time frames of equal duration. It shall be noted that the ADC 132 can be part of or integrated in the microphone 56, or part of a signal processing unit. Understandably, in other embodiments, the in-ear microphone 56 could also directly output a digital signal.

The system 140 typically comprise a signal filtering module 144, the trained classification module (19 or 50) and a calculation module 146, as concurrently presented in FIG. 5. The filtering module 144 receives the digital signal and provides a required time or frequency filtering to enhance the signal-to-noise ratio of the digital signal. Notice that the filtering module 144 can involve a second input from another microphone or pressure sensor, such as an Outer Ear Microphone 182, In a typical embodiment, the Outer Ear Microphone 182 is positioned at the outer faceplate of the in-ear device. The trained classification module (19 or 50) receives the filtered signal, if a nonverbal audio event is detected, the trained classification module (19 or 50) identifies the corresponding audio event. in real-time or identifies the nature of the nonverbal audio event, according to the audio feature parameters of the trained classification module (19 or 50). The filtered signal is then weighted (often simply multiplied, as illustrated) by the value returned by the classification module. The value returned by the classification module is indicative of an artifact to be removed. The resulting signal is typically fed to the calculation module 146. The calculation module 146 is generally configured to compute the RMS energy of the microphone signal 56, without the wearer-induced artefacts. The noise exposure value is then presented to the user or sent to another monitoring device.

Now referring to FIG. 15, an embodiment of silent interface system and method 150 is illustrated. The system 150 allows to use subtle voluntary actions such as explicit tongue and teeth clicking to replace audible verbal commands, or other commands, when necessary in human-machine interactions. Silent interfaces generally aim at providing inconspicuous ways of communication that are not significantly affected by ambient noise and accessible to people with speech impairment.

The silent interface and assistive system 150 comprises an in-ear microphone 56 or pressure sensor. In a typical embodiment, the in-ear microphone 56 is conveniently located inside or at the vicinity of the ear and is adapted to capture sounds present in the open or occluded human ear-canal. The system 150 may further comprise an ADC 152 configured to receive the captured signal and to produce a digital signal having time frames of equal duration. It shall be noted that the ADC 132 can be part of or integrated in the microphone 56, or part of a signal processing unit. Understandably, in other embodiments, the in-ear microphone 56 could also directly output a digital signal.

The system 150 may also comprise a signal filtering module 154, a trained classification module (19 or 50) and a command module 156. The digital signal is filtered by the filtering module 154 according to a required time or frequency filtering in order to enhance the signal-to-noise ratio of the digital signal. Notice that the filtering module 154 can involve a second input from another microphone or pressure sensor, such as an Outer Ear Microphone 182. In a typical embodiment, the Outer Ear Microphone 182 is positioned at the outer faceplate of the in-ear device. The trained classification module (19 or 50) receives the filtered signal and if the filtered signal corresponds to a nonverbal audio event, the trained classification module (19 or 50) identifies the nonverbal audio event or identifies the nature of the nonverbal audio event, in real time, according to the audio feature parameters of the trained classification module (19 or 50). The identified nonverbal audio event is then interpreted by the command module 156. For instance, the command module 156 can be configured or programmed to perform a statistical analysis of the identified nonverbal audio event, in order to provide an accurate assessment of the command. For example, a simple teeth click can correspond to a simple mouse click, a repeated teeth click within a short interval can correspond to a toggle button action, a tongue clicking can prompt an audio menu (played within the digital earplug) that the user can interact with only using simple or double teeth clicking.

Now referring to FIG. 16, an embodiment of biosignal monitoring system and method 160 is illustrated. The identification and extraction of human-produced non-verbal events that result from the physiological activity of nervous system (sympathic and parasympathic systems) enables biosignal (heartbeat and breathing rates) monitoring by properly identifying the rate of occurrences of these biosignal events, an estimate for the individual wearer's health and safety can be performed. Continuous monitoring of theses biosignal characteristics can be performed to possibly diagnostic medical conditions (arrhythmic heartbeat, cardiac coherence, etc.), by comparison to normative data obtained on a group of subjects for a given condition.

The biosignal monitoring system 160 comprises an in-ear microphone 56 or pressure sensor. In a typical embodiment, the in-ear microphone 56 is located inside or at the vicinity of the ear and is configured to capture the sounds present in the open or occluded human ear canal. The system 160 may further comprise an ADC 162 that receives the captured signal and converts it to a digital signal having time frames of equal duration and that are much shorter duration than the time period of the biosignal to be measured. It shall be noted that the ADC 132 can be part of or integrated in the microphone 56, or part of a signal processing unit. Understandably, in other embodiments, the in-ear microphone 56 could also directly output a digital signal.

The system 160 further comprises a signal filtering module 164, the trained classification module (19 or 50), a tracking module 166A and a diagnostic module 166B. The filtering module 164 filters the digital signal to enhance the signal-to-noise ratio. The filtering module 164 can use a second input from another microphone or pressure sensor, such as an Outer Ear Microphone 182. In a typical embodiment, the Outer Ear Microphone 182 is positioned at the outer faceplate of the in-ear device, as presented in FIG. 16. The trained classification module (19 or 50) receives the filtered signal and is configured or programmed to identify nonverbal audio event or biosignal corresponding to the parameters of the filtered signal according to the audio feature parameters of the trained classification module 50. The trained classification module (19 or 50) produces a series of pulses corresponding to the identified biosignal. The tracking module 166A receives the series of pulses and performs a statistical analysis for accurately assessing a pace indicator (heartbeat, breathing rates, etc.) of the biosignal. The diagnostic module 166B receives the series of pulses and the filtered signal and analyses the characteristics in time, frequency and periodicity to detect a potential medical condition. The biosignal pace indicator and the detected potential medical condition are then presented to the user or sent to another monitoring or health interpretation device.

According to another embodiment, as presented in FIG. 17A, there is a method 170 of identifying nonverbal audio events such as mechanically-induced nonverbal audio events. Mechanically-induced nonverbal audio events can be produced by electronic earpiece cable friction on wearer's clothes or taping on the earpiece. Such mechanically-induced nonverbal audio events can be used for a variety of applications, ranging from the removing of these disturbances to control-interfaces, as presented in FIG. 17B.

The method 170 consists of capturing 172 an audio signal from an ear canal of a user and denoising 174 the audio signal. The denoised audio signal is classified 176 with the trained classification module (19 or 50) and depending on the classification a mechanically-induced nonverbal audio event is identified 178. Once identified a corresponding response is provided 179. For instance, as presented in FIG. 17B, an earpiece manipulation producing a cable movement 171A can be detected as a disturbance 178A, as an aging of parts 178B or as a simple movement 178C. A leak or a cracking or ticking of parts 171B can be detected as a disturbance 178A or as an aging of parts 178B. Another manipulation such as an insertion or extraction of an earpiece from a user's ear canal 171C can be detected as a disturbance 178A or an activity or movement 178C, an effective post-insertion or post-extraction 178D or a user interface input 178E. Yet another manipulation such as an earpiece taping such as in a Morse code sequence 171D can be detected as a disturbance 178A, an activity or movement 178C or a user interface input 178E. In response 179 to each detected nonverbal audio event, the method is adapted to for instance adjust a dose computation 179A, adjust an earpiece transfer function 179B, adjust a biosignal computation 179C, indicate that the required specifications are not met 179D, indicate that the user is alive, 179E, trigger a post-insertion action 179F, trigger an audio prompt 179G or control a device behavior 179H.

It shall be recognized that the trained classification module (19 or 50) can be used by a variety of other detection and monitoring applications that rely on captured in-ear audio signals and are required to produce an accurate interpretation of the nonverbal audio event in real time.

Moreover, the use of a variety of signals accessible inside an occluded ear, such as breathing, eye blinking, heart rate and speech, emotion detection of the user can be achieved using a multimodal technique that assesses all these signals together rather than individually.

While illustrative and presently preferred embodiments have been described in detail hereinabove, it is to be understood that the inventive concepts may be otherwise variously embodied and employed and that the appended claims are intended to be construed to include such variations except insofar as limited by the prior art.

The invention claimed is:

1. A method for real time estimation of a noise exposure value in an ear of a user net of user-induced artefacts, the method comprising:
   using a contactless in-ear microphone to capture an in-ear sound pressure present in an inner portion of an occluded ear canal of the user as an in-ear audio signal;
   using an outer-ear microphone to capture an outer-ear sound pressure present at the outer entry of the occluded ear canal as an outer-ear audio signal wherein the outer-ear sound pressure is captured simultaneously to the captured in-ear sound pressure;

denoising the captured in-ear audio signal using the captured outer-ear audio signal;
sampling the in-ear audio signal;
extracting, in real time, user-induced non-verbal audio artefacts of each sample of the in-ear audio signal;
finding a match between each of the extracted user-induced non-verbal audio artefacts with one of a plurality of pre-recorded samples of user-induced artifacts:
subtracting the matching user-induced non-verbal artefact from the simultaneous in-ear audio signal:
estimating in-ear audio signal without user-induced artefacts using the remainder of the simultaneous in-ear audio signal:
calculating, in real-time, the noise-exposure value using the estimated signal.

2. The method of claim 1, wherein the sampling further comprises sampling a frame having a duration ranging between 200 milliseconds and 1200 milliseconds.

3. The method of claim 2 wherein the sampling further comprises sampling a 400 milliseconds frame of the in-ear audio signal.

4. The method of claim 1, wherein finding a match between each of the extracted user-induced non-verbal audio artefacts further comprises comparing the extracted user-induced non-verbal audio artefacts with a plurality of samples of the in-ear audio signal.

5. The method of claim 1, wherein the extracted user induced nonverbal audio artefacts are selected from the group consisting of teeth clicking, tongue clicking, blinking, eye closing, teeth grinding, throat clearing, saliva noise, swallowing, coughing, talking, yawning with inspiration, yawning with expiration, respiration, heartbeat and head or body movement, earpiece manipulation, and any combination thereof.

6. A system for real time estimation of a noise exposure value in an ear canal of a user net of unwanted artefacts, the system comprising:
an electronic earpiece comprising:
an acoustic seal for fully occluding an inner portion of the ear canal of the user;
an in-ear contactless microphone for capturing sound pressure present within the fully occluded inner portion of the ear canal as an in-ear audio signal; and
an outer-ear microphone for capturing sound pressure present at the outer entry of the occluded ear canal as an outer-ear audio signal, wherein the outer-ear microphone is configured to capture the outer-ear sound pressure simultaneously to the captured in-ear sound pressure;
a memory for storing in real time the in-ear audio signal captured by the in-ear microphone;
a data source comprising pre-recorded samples of user-induced artefacts;
a denoiser configured to denoise the in-ear audio signal present in the memory using the simultaneously captured outer-ear audio signal;
an in-ear audio signal sampler:
an audio artefact extraction module for extracting, in real time, user-induced non-verbal audio artefact for each sample of the in-ear audio signal;
a processing unit configured for:
finding a match between each extracted user-induced non-verbal audio artefact with one of the plurality of pre-recorded samples of user-induced artifacts of the data source;
subtracting the matching user-induced non-verbal audio artefact from the simultaneous in-ear audio signal to estimate in-ear audio signal without user-induced artefacts;
calculating, in real-time, the noise-exposure value using the estimated signal and storing the noise exposure value in the memory.

7. The system of claim 6, wherein the processing device is further configured to detect at least one of a health indicator, mood indicator, biosignal indicator, artefact indicator, command indicator, non-user induced event indicator, user induced event indicator.

8. The system of claim 6, wherein the audio artefact extraction module is further configured to determine a nonverbal audio artefact according to an in-ear audio signal captured by a health monitoring system.

9. The system of claim 6, wherein the processing device is further configured to determine a nonverbal audio event according to an in-ear audio signal captured by a biosignal monitoring system.

10. The method of claim 1 wherein the extracting of the user-induced audio artefacts is performed by executing a trained machine learning algorithm.

11. The system of claim 6, the processing device being further configured to execute a machine learning algorithm to perform validation of the extracted user-induced non-verbal audio artefact.

12. The system of claim 6 further comprising an adaptive filter configured to perform the denoising of the captured in-ear audio signal using an estimation of the transfer function of the occluded ear between the outer-ear microphone and the inner-ear microphone.

13. The system of claim 11, the machine learning algorithm being based on a confusion matrix using Gaussian Mixture Models.

14. The system of claim 11, the machine learning algorithm being based on a confusion matrix using a support vector machine.

15. The method of claim 10, the machine learning algorithm using a multi-layer perception neural network.

16. The method of claim 10, the trained machine learning algorithm being based on a confusion matrix using Gaussian Mixture Models.

17. The method of claim 10, the trained machine learning algorithm being based on a confusion matrix using a support vector machine.

18. The method of claim 1, the method further comprising identifying verbal user-induced artefacts from the simultaneous in-ear audio signal using the captured outer-ear audio signal.

19. The method of claim 18, the identification of verbal user-induced artefacts using a transfer function of the occluded ear.

20. The method of claim 18, the method further comprising removing the identified verbal user-induced artefacts from the simultaneous in-ear audio signal.

* * * * *